United States Patent
Hiruma et al.

(10) Patent No.: US 7,348,017 B2
(45) Date of Patent: Mar. 25, 2008

(54) DITHIAZOLE COMPOUNDS, MATRIX METALLOPROTEASE INHIBITORS AND EXTERNAL PREPARATIONS FOR THE SKIN

(75) Inventors: Takuya Hiruma, Yokohama (JP); Koji Kobayashi, Yokohama (JP); Shinji Inomata, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 495 days.

(21) Appl. No.: 10/487,411

(22) PCT Filed: Aug. 28, 2002

(86) PCT No.: PCT/JP02/08649

§ 371 (c)(1),
(2), (4) Date: Feb. 23, 2004

(87) PCT Pub. No.: WO03/020711

PCT Pub. Date: Mar. 13, 2003

(65) Prior Publication Data

US 2004/0236111 A1    Nov. 25, 2004

(30) Foreign Application Priority Data

Aug. 28, 2001 (JP) ............... 2001-258066

(51) Int. Cl.
*A61K 8/02* (2006.01)
*A61K 31/41* (2006.01)
*C07D 285/01* (2006.01)

(52) U.S. Cl. ............. 424/401; 514/360; 548/123

(58) Field of Classification Search ........ 548/123; 514/360; 424/401
See application file for complete search history.

(56) References Cited

U.S. PATENT DOCUMENTS 3,753,908 A    8/1973    de Vries et al.

FOREIGN PATENT DOCUMENTS

| DE | 2 228 364 | | 12/1973 |
|---|---|---|---|
| DE | 2228364 A | * | 12/1973 |
| WO | WO 98/08815 A1 | | 3/1998 |

OTHER PUBLICATIONS

Patani et al. "Bioisosterism: A Rational Approach in Drug Design" Chemical Reviews 1996, vol. 96, pp. 3147-3176.*
Inomata et al. "Possible Involvement of Gelatinases in Basement Membrane Damage and Wrinkle Formation in Chronically Ultraviolet B-exposed Hairless Mouse" The Journal of Investigative Dermatology 2003, vol. 120, No. 1, pp. 1-7.*
Amano et al. "Protective effect of matrix metalloproteinase inhibitors against epidermal basement membrane damage: skin equivalents partially mimic photoageing process" British Journal of Dermatology 2005, vol. 153, Suppl 2, pp. 37-46.*
Gary J. Fisher et al., "Molecular basis of sun-induced premature skin ageing and retinoid antagonism", Nature 1996, vol. 379, pp. 335-339.
Gary J. Fisher et al., "Pathophysiology of Premature Skin Aging Induced by Ultraviolet Light", The New England Journal of Medicine, vol. 337, No. 20, pp. 1419-1428.
Kaori Miyazaki et al. "Matrix metalloproteinases: Their structures and functions, with special reference to their roles in tumor invasion and metastasis", Biochemistry 1996, vol. 68, No. 12, pp. 1791-1807.

* cited by examiner

*Primary Examiner*—Rebecca Anderson
*Assistant Examiner*—Joseph R. Kosack
(74) *Attorney, Agent, or Firm*—Fei-Fei Chao; Andrews Kurth LLP

(57) ABSTRACT

A dithiazole compound or a salt thereof is disclosed. The compound inhibits matrix metalloprotease (MMPs) activity and can be used in pharmaceutical and cosmetic compositions for the treatment of skin conditions.

8 Claims, No Drawings

DITHIAZOLE COMPOUNDS, MATRIX METALLOPROTEASE INHIBITORS AND EXTERNAL PREPARATIONS FOR THE SKIN

RELATED APPLICATIONS

This application claims priority to Japanese Patent Application No. 2001-258066 filed on Aug. 28, 2001, which is incorporated herein by reference.

FIELD OF THE INVENTION

The present invention relates to a dithiazole compound and, in particular, to a matrix metalloproteases (MMPs) inhibitor.

BACKGROUND OF THE INVENTION

A human skin is roughly classified into three layers of epidermis, dermis and subcutaneous tissue, and epidermis and dermis are contacted each other through a basement membrane.

An epidermic cell contacting with the basement membrane repeats division without cease, and the divided epidermic cells are successively pushed upward to form stratum corneum, which is the uppermost layer of epidermis, via differentiation. Stratum corneum is an extremely important site from a viewpoint of beauty. Since the basement membrane structure has great influence on division of epidermic cells, it can be said that the basement membrane also has great influence on a skin.

The basement membrane is one of extracellular matrices, and is composed of type IV collagen, proteoglycan, laminin, fibronectin and the like.

An extracellular space in dermis is filled mainly with a network structure of a huge macromolecule called extracellular matrix (ECM). The ECM is composed of fibrous proteins such as collagen, elastin, fibronectin, laminin and the like, and polysaccharides called glycosaminoglycan or proteoglycan. Due to such the structure, dermis has great influence on elasticity and tension of a skin.

Up to now, it has been known that ultraviolet ray is greatly involved in changes of a skin accompanied with aging, that are, wrinkles, dullness, lost of texture, reduction in elasticity and the like. When these changes are observed microscopically, in dermis, ECM components such as collagen, elastin and the like are reduced and denatured and, further, damage of a basement membrane and thickening of epidermis occur.

With progress of recent study, as a factor inducing these changes, in particular, involvement of matrix metalloproteases (MMPs) is pointed out. MMPs is a generic name of a group of metalloproteases which main substrate is an extracellular matrix protein. Many kinds of MMPs are known, and they have common structural or functional characteristics, but their substrate proteins are different from each other (Kaori Miyazaki et al. "Biochemistry", vol. 68, No. 12, pp. 1791-1807 (1996)).

MMPs are usually classified into collagenase group, gelatinase group, stromlycin group, and others (matrilycin etc.) in view of their structures and functions.

The collagenase group includes MMP-1 (interstitial collagenase), MMP-8, MMP-13 and the like. Inter alia, MMP-1 is known to be an enzyme degrading type I collagen, type III collagen and the like, which are main components of dermis matrix. Also, MMP-8 and MMP-13 have the action of degrading type I collagen and the like.

The gelatinase group includes MMP-2, MMP-9 and the like. MMP-2 and MMP-9 are known to be an enzyme degrading type IV collagen and laminin which are basement membrane components, and degrading elastin and the like which are dermis matrix components.

The stromlycin group includes MMP-3, MMP-10 and the like. MMP-3 and MMP-10 are known to be an enzyme degrading proteoglycan, type IV collagen, laminin and the like.

Also, expressions of these respective enzymes are greatly increased by irradiation of ultraviolet ray, which becomes one cause of reduction and denaturation in ECM by ultraviolet ray. This is thought to be one great factor for wrinkle-formation and the like on a skin (Gary J. Fisher et al., "Nature", 379 (25), 335(1996); Gary J. Fisher et al, "The New England Journal of Medicine", 337(20), 1419(1997)).

Therefore, it is considered that inhibition of MMPs activity is important in protecting the basement membrane and various extracellular matrices, and improving or preventing skin aging such as wrinkles and slacks. Thus, excellent MMPs inhibiting substances are desired.

In addition, since MMPs are involved in tissue matrix degradation as described above, it is suggested that MMPs are involved in many disease states accompanying abnormal metabolism of a connecting tissue or a basement membrane matrix, for example, arthritis (rheumatoid arthritis, osteoarthritis etc.), bone disease (osteoporosis etc.), periodontal disease, ectopic angiogenesis, multiple sclerosis, metastasis of tumor, and tissue ulcer formation (ulcer formation of cornea, epidermis, stomach etc.) (WO 98/08815 etc.). Therefore, MMPs inhibitor is also expected as an agent for treating or preventing these diseases due to abnormal metabolism of tissue matrix.

SUMMARY OF THE INVENTION

An object of the present invention is to provide a compound having the MMPs inhibiting action, and to provide a MMPs inhibitor, a pharmaceutical composition, a cosmetic composition and a skin external composition containing the same as an active ingredient.

In order to solve the aforementioned problems, the present inventors intensively studied and, as a result, found that a particular dithiazole compound has an excellent MMPs inhibiting action, which resulted in completion of the present invention.

That is, the dithiazole compound of the present invention is expressed by the following formula (I):

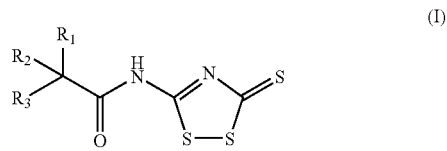

wherein $R_1$ is hydrogen atom, alkyl, alkenyl, aryl, arylalkyl, heteroarylalkyl, heteroarylthioalkyl, hydroxy, alkoxyalkyl or Het-alkyl (wherein Het is 5-or 6-membered heterocyclic group containing at least one nitrogen atom, and said nitrogen atom is bonded to the alkyl group);

$R_2$ is hydrogen atom, alkyl, aryl, arylalkyl, heteroaryl, heteroarylalkyl, hydroxy, alkoxy, $H(C_xH_{2x}O)_m$— (wherein x is an integer of 1 to 3, and m is an integer of 2 to 5), arylalkoxy, hydroxyalkyl, acyloxyalkyl, alkoxyalkyl, (aryl or heteroaryl)-alkoxyalkyl, alkyl-(thio, sulfinyl or sulfonyl)- alkyl, (amino or alkylamino)-alkyl, acylaminoalkyl, amino, alkylamino, acylamino or Het-alkyl; and $R_3$ is a group expressed by the following formula (II), (III) or (IV):

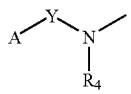

(II)

wherein A is alkyl, alkoxy, aryl, aryloxy, heteroaryl, aryl-$Z_1$-aminoaryl or arylamino-$Z_1$-aryl;

Y and $Z_1$ are each —$SO_2$— or —CO—;

$R_4$ is hydrogen atom, alkyl, aryl, arylalkyl, heteroaryl, heteroarylalkyl, hydroxyalkyl, acyloxyalkyl, alkoxyalkyl, alkyl-(thio, sulfinyl or sulfonyl)-alkyl, (amino or alkylamino)-alkyl or acylaminoalkyl; and wherein the group A—Y—N ($R_4$)—$CR_1R_2$—CONH— may be a group expressed by the following formula (II'):

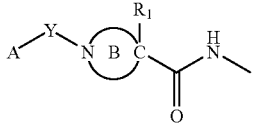

(II')

wherein the ring B is 1,2,3,4-tetrahydroisoquinoline, piperidine, oxazolidine, thiazolidine, pyrrolidine, morpholine piperazine or thiomorpholine, and A, Y and $R_1$ are as defined above;

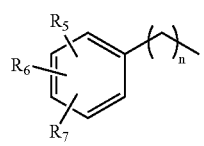

(III)

wherein $R_5$, $R_6$ and $R_7$ are each hydrogen atom, alkyl, alkenyl, aryl, heteroaryl, arylalkyl, heteroarylalkyl, halogen atom, amino, alkylamino, (aryl or heteroaryl)-amino, (aryl or heteroaryl)-alkylamino, acylamino, (alkyl, aryl or heteroaryl)-$Z_2$-amino, hydroxy, alkoxy, $H(C_xH_{2x}O)_m$— (wherein x is an integer of 1 to 3, and m is an integer of 2 to 5), alkenyloxy, aryloxy, heteroaryloxy, acyl, acyloxy, (aryl or heteroaryl)-alkoxy, (alkyl, aryl or heteroaryl)-$Z_3$-oxy, mercapto, alkylthio, arylthio, heteroarylthio, acylthio, (aryl or heteroaryl)-alkylthio or (alkyl, aryl or heteroaryl)-$Z_4$-thio;

$Z_2$, $Z_3$ and $Z_4$ are each —$SO_2$— or —CO—;

n is 0 or 1; and wherein when n=1, the compound (I) may be a compound expressed by the following formula (I'):

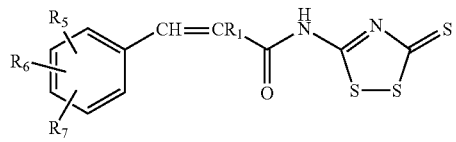

(I')

wherein $R_1$, $R_5$, $R_6$ and $R_7$ are as defined above;

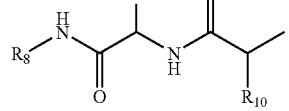

(IV)

wherein $R_8$ is hydrogen atom or alkyl; $R_9$ is a side chain of an α-amino acid; and $R_{10}$ is hydrogen atom, alkyl, alkenyl or arylalkyl.

In the compound (I) of the present invention, it is preferable that: $R_1$ is hydrogen atom or alkyl; $R_2$ is hydrogen atom, hydroxy, alkyl, alkoxy, $H(C_xH_{2x}O)_m$—, aryl, arylalkoxy, arylalkyl, heteroarylalkyl, Het-alkyl or alkylamino; and $R_3$ is any one of said groups (II) to (IV);

wherein when $R_3$ is said group (II), A is aryl or aryl-$Z_1$-aminoaryl, Y and $Z_1$ are each —$SO_2$— or —CO—, and $R_4$ is hydrogen atom, arylalkyl or heteroarylalkyl, or the group A-Y—N($R_4$)—$CR_1R_2$—CONH— may be said group (II');

wherein when $R_3$ is said group (III), $R_5$, $R_6$ and $R_7$ are each hydrogen atom, alkyl, alkoxy, $H(C_xH_{2x}O)_m$—, alkenyloxy, arylalkoxy, heteroarylalkoxy, aryl-$Z_2$-amino, alkylamino, arylamino or heteroarylamino, and n is 0 or 1, wherein when n=1, the compound (I) may be said compound (I');

wherein when $R_3$ is said group (IV), $R_8$ is hydrogen atom or alkyl, $R_9$ is a side chain of an α-amino acid, and $R_{10}$ is hydrogen atom or alkyl.

When $R_3$ is said group (II) in the compound (I), it is preferable that $R_1$ is hydrogen atom, and Y is —$SO_2$—. A is preferably alkoxyphenyl or (alkylbenzoyl)aminophenyl. $R_2$ is preferably hydrogen atom, alkyl, arylalkyl or heteroarylalkyl. It is also preferable that the group A-Y—N($R_4$)—$CR_1R_2$—CONH— is said group (II'), and the ring B is 1,2,3,4-tetrahydroisoquinoline, pyrrolidine or morpholine.

When $R_3$ is said group (III) in the compound (I), it is preferable that $R_1$ is hydrogen atom or alkyl, and n is 0. $R_2$ is preferably hydrogen atom, hydroxy, alkyl, alkoxy, $H(C_xH_{2x}O)_m$—, aryl, arylalkoxy or alkylamino. It is preferable that $R_5$ is hydrogen atom, $R_6$ is hydrogen atom, alkoxy or arylalkoxy, and $R_7$ is alkoxy, alkenyloxy or arylalkoxy. It is also preferable that the compound (I) is expressed by said formula (I'), wherein $R_1$, $R_5$ and $R_6$ are each hydrogen atom and $R_7$ is arylalkoxy.

When $R_3$ is said group (IV) in the compound (I), it is preferable that $R_1$ is hydrogen atom, $R_2$ is hydrogen atom or Het-alkyl, $R_8$ is alkyl, $R_9$ is alkyl or arylalkyl, and $R_{10}$ is alkyl.

A matrix metalloprotease-inhibitor of the present invention comprises, as an active ingredient, said dithiazole compound or the pharmacologically acceptable salt thereof.

A cosmetic composition of the present invention comprises, as an active ingredient, said dithiazole compound or the pharmacologically acceptable salt thereof.

A pharmaceutical composition of the present invention comprises, as an active ingredient, said dithiazole compound or the pharmacologically acceptable salt thereof.

A skin external composition of the present invention comprises, as an active ingredient, said dithiazole compound or the pharmacologically acceptable salt thereof.

BEST MODE FOR CARRYING OUT THE INVENTION

In the present invention, $R_1$ can be hydrogen atom, alkyl, alkenyl, aryl, arylalkyl, heteroarylalkyl, heteroarylthioalkyl, hydroxy, alkoxyalkyl or Het-alkyl, preferably hydrogen atom or alkyl, further preferably hydrogen atom.

$R_2$ can be hydrogen atom, alkyl, aryl, arylalkyl, heteroaryl, heteroarylalkyl, hydroxy, alkoxy, $H(C_xH_{2x}O)_m$—, arylalkoxy, hydroxyalkyl, acyloxyalkyl, alkoxyalkyl, (aryl or heteroaryl)-alkoxyalkyl, alkyl-(thio, sulfinyl or sulfonyl)-alkyl, (amino or alkylamino)-alkyl, acylaminoalkyl, amino, alkylamino, acylamino or Het-alkyl. It is preferably hydrogen atom, hydroxy, alkyl, alkoxy, $H(C_xH_{2x}O)_m$—, aryl, arylalkoxy, arylalkyl, heteroarylalkyl, Het-alkyl or alkylamino.

In the group $H(C_xH_{2x}O)_m$— of the present invention, x is an integer of 1 to 3, m is an integer of 2 to 5, and each $(C_xH_{2x}O)$ unit may be the same or different from each other.

$R_3$ is any one of the aforementioned groups (II) to (IV).

When $R_3$ is said group (II), $R_1$ is preferably hydrogen atom. $R_2$ is preferably hydrogen atom, alkyl, arylalkyl or heteroarylalkyl. The alkyl is preferably isopropyl, and the arylalkyl is preferably benzyl. The heteroarylalkyl is preferably indolylmethyl.

A can be alkyl, alkoxy, aryl, aryloxy, heteroaryl, aryl-$Z_1$-aminoaryl or arylamino-$Z_1$-aryl (wherein $Z_1$ can be —$SO_2$— or —CO—). A is preferably unsubstituted or alkoxy-substituted aryl, or unsubstituted or alkyl-substituted aryl-$Z_1$-aminoaryl, more preferably phenyl, alkoxyphenyl, benzoylaminophenyl or alkylbenzoylaminophenyl, particularly preferably methoxyphenyl or methylbenzoylaminophenyl.

Y is —$SO_2$— or —CO—, preferably —$SO_2$—.

$R_4$ can be hydrogen atom, alkyl, aryl, arylalkyl, heteroaryl, heteroarylalkyl, hydroxyalkyl, acyloxyalkyl, alkoxyalkyl, alkyl-(thio, sulfinyl or sulfonyl)-alkyl, (amino or alkylamino)-alkyl or acylaminoalkyl, preferably hydrogen atom, arylalkyl or heteroarylalkyl. The arylalkyl is preferably benzyl, and the heteroarylalkyl is preferably pyridinylmethyl.

In addition, the group A-Y—N($R_4$)—$CR_1R_2$—CONH— can be said group (II'). The ring B in said group (II') is 1,2,3,4-tetrahydroisoquinoline, piperidine, oxazolidine, thiazolidine, pyrrolidine, morpholine, piperazine or thiomorpholine, preferably 1,2,3,4-tetrahydroisoquinoline, pyrrolidine or morpholine. The ring B may be substituted with an alkyl at any position. When the ring B is a piperazine ring, a nitrogen atom which is not bonded to Y may be substituted with alkyl, acyl, alkylsulfonyl, (aryl or heteroaryl)-carbonyl, alkylsulfonyl, (aryl or heteroaryl)-sulfonyl or alkoxycarbonyl.

When $R_3$ is said group (III), $R_1$ is preferably hydrogen atom or alkyl. The alkyl is preferably methyl. $R_1$ is particularly preferably hydrogen atom.

In addition, $R_2$ is preferably hydrogen atom, hydroxy, alkyl, $H(C_xH_{2x}O)_m$—, aryl, arylalkoxy or alkylamino. The alkyl is preferably methyl or isopropyl. A group represented by $H(C_xH_{2x}O)_m$— is preferably a group wherein x is 1 or 2, and m=3, further preferably methoxyethoxymethoxy group. The aryl is preferably unsubstituted or haloarylalkoxy-substituted phenyl, further preferably fluorobenzyloxyphenyl. The arylalkoxy is preferably benzyloxy. The alkylamino is preferably dimethylamino. $R_2$ is particularly preferably hydrogen atom or alkyl.

Each of $R_5$, $R_6$ and $R_7$ can be hydrogen atom, alkyl, alkenyl, aryl, heteroaryl, arylalkyl, heteroarylalkyl, halogen atom, amino, alkylamino, (aryl or heteroaryl)-amino, (aryl or heteroaryl)-alkylamino, acylamino, (alkyl, aryl or heteroaryl)-$Z_2$-amino, hydroxy, alkoxy, $H(C_xH_{2x}O)_m$—, alkenyloxy, aryloxy, heteroaryloxy, acyl, acyloxy, (aryl or heteroaryl)-alkoxy, (alkyl, aryl or heteroaryl)-$Z_3$-oxy, mercapto, alkylthio, arylthio, heteroarylthio, acylthio, (aryl or heteroaryl)-alkylthio or (alkyl, aryl or heteroaryl)-$Z_4$-thio. Each of $Z_2$, $Z_3$ and $Z_4$ represents —$SO_2$— or —CO—.

Each of $R_5$, $R_6$ and $R_7$ is preferably hydrogen atom, alkyl, alkoxy, $H(C_xH_{2x}O)_m$—, alkenyloxy, arylalkoxy, heteroarylalkoxy, aryl-$Z_2$-amino, alkylamino, arylamino or heteroarylamino. Further, it is preferable that $R_5$ is hydrogen atom, $R_6$ is hydrogen atom, alkoxy or arylalkoxy, and $R_7$ is alkoxy, alkenyloxy or arylalkoxy.

In $R_5$ to $R_7$, the alkyl is preferably propyl, and the alkoxy is preferably methoxy or octyloxy. The $H(C_xH_{2x}O)_m$— is preferably the group wherein x=2 and m=3. The alkenyloxy is preferably geranyloxy. The arylalkoxy is preferably unsubstituted or halogen-, alkoxy- or arylalkoxy-substituted benzyloxy, further preferably fluorobenzyloxy, methoxybenzyloxy or (benzyloxy)benzyloxy. The heteroarylalkoxy is preferably pyridinylmethyloxy. The aryl-$Z_2$-amino is preferably unsubstituted or alkoxy-substituted phenyl-$Z_2$-amino, and further preferably methoxyphenylsulfonylamino or butoxyphenylcarbonylamino. The alkylamino is preferably butylamino. The arylamino is preferably anilino, and the heteroarylamino is preferably pyridinylamino.

n is 0 or 1, preferably 0. When n=1, the compound (I) may be the compound (I'). In the compound (I'), $R_1$, $R_5$, $R_6$ and $R_7$ are as defined above. It is preferable that $R_1$, $R_5$ and $R_6$ are hydrogen atoms and $R_7$ is unsubstituted or halogen-substituted arylalkoxy, further fluorobenzyloxy.

When $R_3$ is said group (IV), $R_1$ is preferably hydrogen atom. $R_2$ is preferably hydrogen atom or Het-alkyl, and said Het-alkyl is preferably a group (H2) described later.

$R_8$ is hydrogen atom or alkyl, preferably alkyl, further preferably methyl.

$R_9$ is a side chain of an α-amino acid, and is derived from a side chain R of an α-amino acid $H_2N$—CH(R)—COOH which can be used as a raw material for an amine $R_8$—NHCO—CH($R_9$)—$NH_2$ in Reaction 15 of Scheme 4 described later. $R_9$ is preferably alkyl or arylalkyl, more preferably tert-butyl or benzyl.

$R_{10}$ is hydrogen atom, alkyl, alkenyl or arylalkyl, preferably alkyl, more preferably isobutyl.

In the present invention, unless otherwise indicated, definition of each group is as follows:

"Alkyl" is a straight, branched or cyclic saturated hydrocarbon group having a carbon number of 1 to 10, preferably a carbon number of 1 to 6. Examples thereof include methyl, ethyl, n-propyl, isopropyl, n-butyl, isobutyl, sec-butyl, tert-butyl, n-pentyl, isoamyl, n-hexyl, n-octyl, cyclopropyl, cyclobutyl, cyclopentyl and cyclohexyl groups.

These alkyl groups may be substituted with one or more substituents selected from halogen atom, hydroxy, carboxy, alkoxycarbonyl, nitro and cyano at any position.

"Alkenyl" means a straight, branched or cyclic unsaturated hydrocarbon group having at least one double bond at any position and having a carbon number of 2 to 10. Examples thereof include vinyl, 1-propenyl, 1-butenyl, 2-butenyl, 2-methyl-2-propenyl, 3,7-dimethyl-2,6-octadienyl(geranyl), cyclopropenyl, cyclobutenyl, cyclopentenyl and cyclohexenyl.

These alkenyl groups may be substituted with one or more substituents selected from aryl, heteroaryl, hydroxy, alkoxy, halogen atom, carboxy, alkoxycarbonyl, nitro, cyano and amino at any position.

"Acyl" represents a carbonyl group having an alkyl or alkenyl group. Examples thereof include acetyl, propionyl, butyryl, acryl and butenoyl groups.

"Acyloxy" is an oxy group having an acyl group.

"Acylamino" is an amino group having an acyl group.

"Acylaminoalkyl" is an alkyl group substituted with an acylamino group.

"Alkoxy" is an oxy group having an alkyl group.

"Alkenyloxy" is an oxy group having an alkenyl group.

"Alkoxyalkyl" is an alkyl group substituted with an alkoxy group.

"Acyloxyalkyl" is an alkyl group substituted with an acyloxy group.

"Alkylamino" is an amino group substituted with one or two alkyl groups.

"Alkylaminoalkyl" is an alkyl group substituted with an alkylamino group.

"Alkylthio" is a thio group having an alkyl group.

"Acylthio" is a thio group having an acyl group.

"Alkylsulfonylamino" is a sulfonylamino group (—SO$_2$NH—) having an alkyl group.

"Alkylthioalkyl" is an alkyl group substituted with an alkylthio group.

"Alkylsulfinylalkyl" is an alkyl group substituted with a sulfinyl group (—SO—) having an alkyl group.

"Alkylsulfonylalkyl" is an alkyl group substituted with a sulfonyl group (—SO$_2$—) having an alkyl group.

"Aryl" is an aromatic hydrocarbon group. Preferable examples thereof include phenyl and naphthyl.

The aryl group may be substituted with one or more substituents selected from alkyl, hydroxy, alkoxy, arylalkoxy, haloarylalkoxy, mercapto, alkylthio, halogen atom, acyl, carboxy, alkoxycarbonyl, nitro, cyano, haloalkyl, aryl, aryloxy, heteroaryl, heteroaryloxy, amino, alkylamino, alkenyl, alkanoyl, acyloxy, acylamino and alkylsulfonyl at any position. Such substituent is preferably alkyl, alkoxy, arylalkoxy, haloarylalkoxy or halogen atom, more preferably methyl, methoxy, butoxy, benzyloxy, fluorobenzyloxy or fluorine atom.

"Arylamino" is an amino group substituted with one or more aryl groups.

"Aryloxy" is an oxy group having an aryl group.

"Arylalkyl" is an alkyl group substituted with an aryl group, preferably benzyl.

"Arylalkoxy" is an alkoxy group substituted with an aryl group, preferably benzyloxy.

"Arylalkoxyalkyl" is an alkyl group substituted with an arylalkoxy group.

"Arylalkylamino" is an amino group substituted with one or more arylalkyl groups.

"Arylthio" is a thio group having an aryl group.

"Arylalkylthio" is an alkylthio group substituted with an aryl group.

"Arylsulfonylamino" is sulfonylamino group (—SO$_2$NH—) having an aryl group.

"Heteroaryl" means a 5- to 10-membered monocyclic or bicyclic aromatic heterocyclic group. Examples thereof include thienyl, furyl, pyrrolyl, pyridinyl, pyrazinyl, thiazolyl, pyrimidinyl, quinolinyl, tetrazolyl, benzothiazolyl, benzofuryl and indolyl. Preferable example is pyridinyl or indolyl.

The heteroaryl may be substituted with one or more substituents selected from alkyl, hydroxy, alkoxy, mercapto, alkylthio, halogen atom, carboxy, alkoxycarbonyl, nitro, cyano, haloalkyl, aryl, aryloxy, heteroaryl, heteroaryloxy, amino, alkylamino, alkenyl, alkanoyl, acyloxy, acylamino and alkylsulfonyl at any position.

"Heteroarylalkyl" is an alkyl group substituted with a heteroaryl group. It is preferably pyridinylmethyl or indolylmethyl.

"Heteroaryloxy" is an oxy group substituted with a heteroaryl group.

"Heteroarylalkoxy" is an alkoxy group substituted with a heteroaryl group. It is preferably pyridinylmethyloxy group.

"Heteroarylalkoxyalkyl" is an alkyl group substituted with a heteroarylalkoxy group.

"Heteroarylamino" is an amino group substituted with one or two heteroaryl groups.

"Heteroarylalkylamino" is an amino group substituted with one or two heteroarylalkyl groups.

"Heteroarylthio" is a thio group having a heteroaryl group.

"Heteroarylalkylthio" is an alkylthio group substituted with a heteroaryl group.

"Heteroarylthioalkyl" is an alkyl group substituted with a heteroarylthio group.

"Heteroarylsulfonylamino" is a sulfonylamino group (—SO$_2$NH—) having a heteroaryl group.

"Halo" and "halogen atom" are each chlorine, bromine, fluorine or iodine atom.

"Haloarylalkoxy" is an alkoxy group having an aryl group substituted with a halogen atom.

"Het" is a 5- or 6-membered monovalent heterocyclic group having at least one nitrogen atom, and said nitrogen atom is bonded to an alkyl group to form "Het-alkyl". Het may contain one or more additional hetero atoms (N, O or S) in addition to the nitrogen atom bonded to the alkyl group. Also, any carbon atom that forms the ring may be substituted with an alkyl or oxo group. When the additional nitrogen atom is present therein, the nitrogen atom may be substituted with an alkyl group. Het may be condensed with an aryl group.

Examples of Het include morpholino, thiomorpholino, piperidino, pyrrolidino and the following groups (H1) to (H3). Preferably, it is the group (H2).

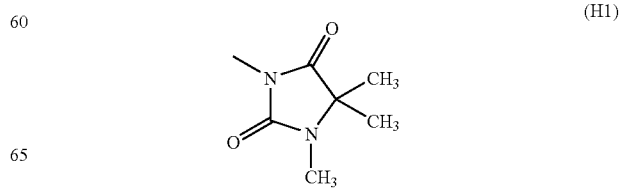
(H1)

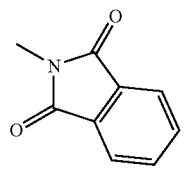

(H2)

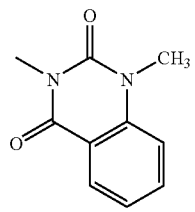

(H3)

The dithiazole compound (I) of the present invention may have one or more asymmetric centers therein. The present compound may be an enantiomer, a diastereomer or a mixture thereof based on an asymmetric carbon. In addition, when there are other isomers such as a conformational isomer and a geometrical isomer, these can be also included in the present invention.

Hereinafter, a representative process for preparing the dithiazole compound (I) is exemplified, and the present invention is not limited thereto. In the following process, unless explicitly indicated, $R_1$ to $R_{10}$, A, Y and n are as defined above. In addition, in each process, if necessary, protecting and deprotecting reactions for an arbitral functional group can be performed at a suitable step.

Among the present compounds, a compound (V) wherein $R_3$ is the group (II) can be synthesized as follows:

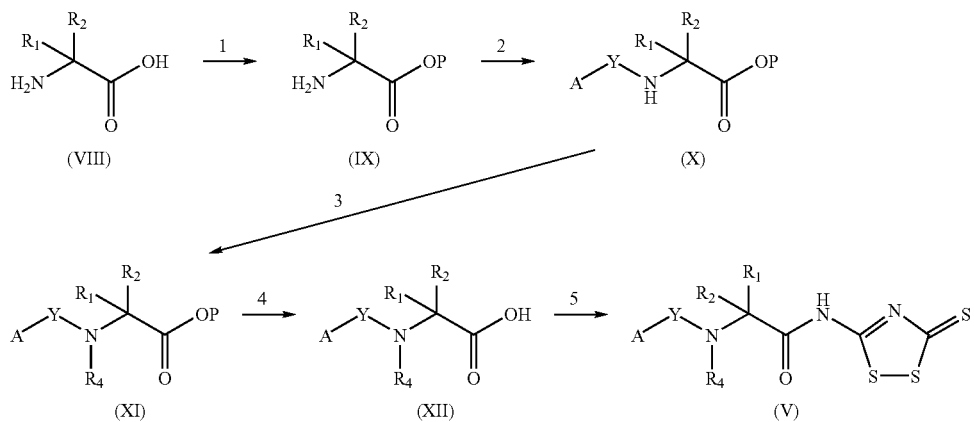

Scheme 1

"Het-alkyl" is an alkyl group having a Het group.

"Side chain of α-amino acid" means a group R of a natural or unnatural α-amino acid represented by $H_2N$—CH(R)—COOH. Examples of the group R of a natural α-amino acid include (corresponding α-amino acid is indicated in parentheses): hydrogen (glycine), methyl (alanine), isopropyl (valine), isobutyl (leucine), hydroxymethyl (serine), 1-hydroxyethyl (threonine), mercaptomethyl (cysteine), 2-methylthioethyl (methionine), carboxymethyl (aspartic acid), carboxyethyl (glutamic acid), 4-aminobutyl (lysine), benzyl (phenylalanine) and p-hydroxybenzyl (tyrosine). Examples of the group R of an unnatural α-amino acid include alkyl groups such as ethyl, n-butyl, t-butyl, neopentyl, n-heptyl and cyclohexylmethyl, phenyl, 1-naphthyl, 2-naphthyl and arylalkyl groups such as phenethyl. When a functional group is present in R, the functional group may be protected with a known protecting group.

In Reaction 1 of Scheme 1, an amino acid (VIII) or an acid-added salt thereof (e.g. hydrochloride) can be esterified using lower alkanol (e.g. methanol), for example, in the presence of thionyl chloride, to give a compound (IX) (wherein P is a protecting group). Alternatively, the reaction may be performed in lower alkanol (e.g. methanol) in the presence of an acid catalyst (e.g. sulfuric acid), if necessary, by heating, to give the compound (IX). Examples of the protecting group P for a carboxyl group include methyl, ethyl, tert-butyl and benzyl. The amino acid (VIII) or an acid-added salt thereof, and the compound (IX) having the protecting group P can be commercially available, or may be synthesized by appropriately combining known methods.

In Reaction 2, the compound (IX) can be subjected to a reaction using a corresponding halide (e.g. A-Y—Cl), specifically, a sulfonylating reagent (e.g. arylsulfonyl chloride) or a carbonilating reagent (e.g. arylcarbonyl chloride) in a solvent (e.g. tetrahydrofuran, toluene or acetonitrile) in the presence of a suitable base (e.g. triethylamine or N-methylmorpholine), to give a compound (X). The sulfonylating reagent can be commercially available, or can be synthesized according to the known method (New Experimental Chemical Course, vol. 14, p.1787(1978) etc.). The carbonilating reagent can be also commercially available, or can be synthesized according to the known method (New Experimental Chemical Course, vol. 14, p.1106(1978) etc.). When the substituent A has a functional group, the substituent A may be further modified at this stage.

In Reaction 3, a reaction can be performed using $R_4$—X (X is halogen such as Cl, Br, I etc.) in a polar solvent (e.g. dimethylformamide) in the presence of a suitable base (e.g. sodium hydride or potassium carbonate), to give a compound (XI). When $R_4$ is hydrogen atom, the compound (X) may be subjected to Reaction 4 without performing Reaction 3.

In Reaction 4, carboxylic acid (XII) can be obtained by using a standard mild method of ester hydrolysis.

In Reaction 5, the carboxylic acid (XII) or its activated compound can be condensed with 3-amino-1,2,4-dithiazole-5-thione represented by the following formula (XIII), to give a compound (V).

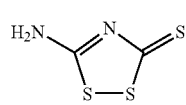

Examples of the activated compound of the carboxylic acid (XII) include an acid anhydride (in particular, mixed acid anhydride), an acid halide and an activated ester. The mixed acid anhydride can be prepared, for example, using pivalic acid chloride or ethyl chlorocarbonate. The acid halide is preferably acid chloride, and can be prepared, for example, using thionyl chloride or oxalyl chloride. The activated ester can be prepared, for example, using 1,1'-carbonyldiimidazole, N-(dimethylaminopropyl)-N'-ethyl-carbodiimide or dicyclohexylcarbodiimide, in the presence or the absence of 1-hydroxybenzotriazole.

A reaction of the activated compound of the carboxylic acid (XII) such as an acid chloride or an activated ester with 3-amino-1,2,4-dithiazole-5-thione (XIII) can be performed in a solvent (e.g. dimethylformamide, tetrahydrofuran or dichloromethane) in the presence of a base (e.g. triethylamine).

Scheme 2

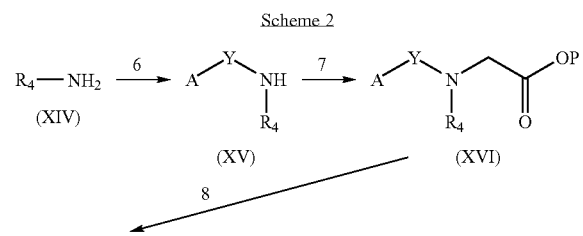

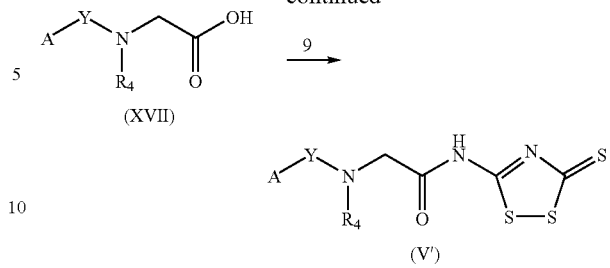

Scheme 2 is an alternative method of Scheme 1, and a compound (V') wherein $R_1$ and $R_2$ of the compound (V) are hydrogen can be synthesized.

In Reaction 6, a reaction can be performed using an amine (XIV) and a corresponding halide (e.g. A-Y—Cl), specifically, a sulfonylating reagent (e.g. arylsulfonyl chloride) or a carbonilating reagent (e.g. arylcarbonyl chloride) in a solvent (e.g. tetrahydrofuran, toluene or acetonitrile) in the presence of a suitable base (e.g. triethylamine), to give a compound (XV).

In Reaction 7, the compound (XV) and alkyl haloacetate (e.g. ethyl bromoacetate) can be reacted in a solvent (tetrahydrofuran, toluene or acetonitrile) in the presence of a base (e.g. sodium hydride), to give a compound (XVI).

Reaction 8 and Reaction 9 can be performed according to said Reaction 4 and Reaction 5 in Scheme 1.

Among the present compounds, a compound (VI) wherein $R_3$ is a group (III) can be prepared as follows:

Scheme 3

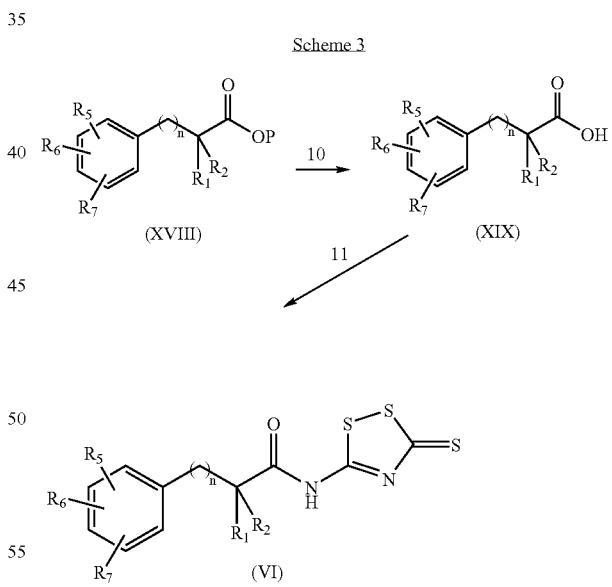

In Scheme 3, Reaction 10 and Reaction 11 can be performed according to said Reaction 4 and Reaction 5 in Scheme 1. The compound (XVIII) can be commercially available, or can be synthesized by appropriately combining known reactions to perform introduction and conversion of a substituent.

Among the present compounds, a compound wherein $R_3$ is the group (IV) and $R_2$ is hydrogen atom can be prepared as follows:

Scheme 4

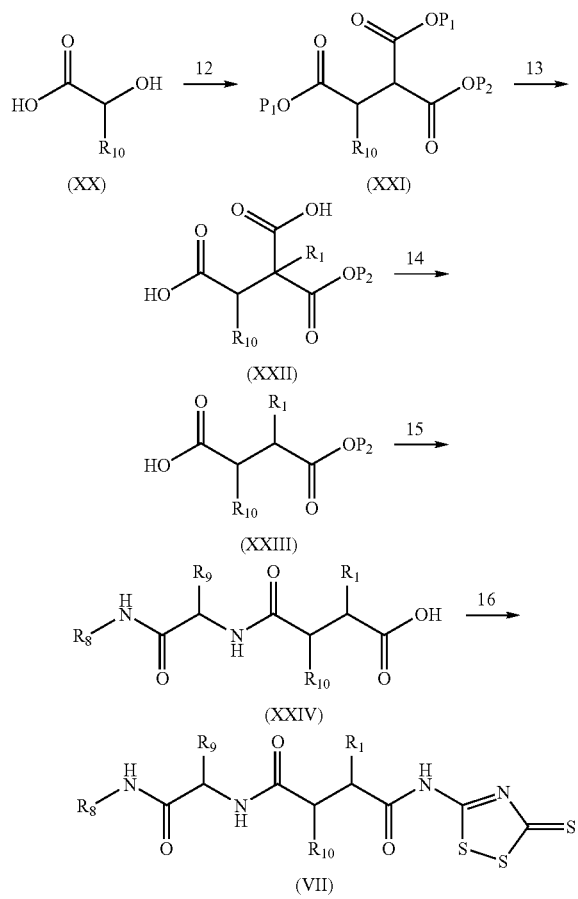

In Reaction 12 of Scheme 4, triester (XXI) can be obtained by protecting a carboxyl group of a hydroxycarboxylic acid (XX) with $P_1$, and converting its hydroxy group into a group having a high eliminating ability such as p-toluenesulfonyloxy, methanesulfonyloxy or trifluoromethansulfonyloxy group, which is reacted with a nucleophilic reagent such as malonate. $P_1$ and $P_2$ mean carboxyl-protecting groups, for example, $P_1$ represents benzyl group, and $P_2$ represents tert-butyl group.

In Reaction 13, using a base (e.g. sodium hydride) and $R_1$—X (X is as defined above), $R_1$ can be introduced into the compound (XXI). Then, a deprotecting reaction, for example, a hydrogenating reaction using a palladium catalyst (Pd—C, Pd—$CaCO_3$ etc.) can be performed to give a dicarboxylic acid (XXII).

In Reaction 14, for example, a decarbonilating reaction can be performed in toluene in the presence of N-methylmorpholine, if necessary, by heating, to give a compound (XXIII).

In Reaction 15, an amidation with an amine ($R_8$—NHCO—CH($R_9$)$NH_2$) is performed in the presence of a condensing agent. The reaction can be performed using a condensing agent such as 1,1'-carbonyldiimidazole, N-(dimethylaminopropyl)-N'-ethylcarbodiimide or dicyclohexylcarbodiimide in a solvent (e.g. dimethylformamide or dichloromethane) in the presence or the absence of 1-hydroxybenzotriazole, preferably at room temperature. Then, by a deprotecting reaction, a carboxylic acid (XXIV) can be obtained.

Reaction 16 can be performed according to the Reaction 5 of Scheme 1.

Starting materials and reagents used in the above Schemes 1 to 4, unless otherwise indicated, can be commercially available, or can be synthesized by appropriating combining known methods.

Depending on a selection of the starting material and method, these compounds may be in the form of one of possible isomers or a mixture thereof, for example, a pure geometrically isomer (cis or trans), an optical isomer (enantiomer), a racemic body or a mixture thereof. The aforementioned possible isomers or a mixture thereof are within the scope of the present invention.

In addition, when a resulting compound is a mixture of isomers, the mixture can be separated into one pure isomer or a racemic body based on a physicochemical difference of components, for example, by chromatography and/or fractional crystallization.

The dithiazole compound of the present invention can be converted into an acid-added salt by a conventional method, if necessary. Examples of an acid of the acid-added salt include inorganic acids such as hydrochloric acid, hydrobromic acid, sulfuric acid and phosphoric acid, and organic acids such as acetic acid, propionic acid, citric acid, lactic acid, oxalic acid, maleic acid, fumaric acid, succinic acid, tartaric acid and methanesulfonic acid.

Since the dithiazole compound (I) of the present invention has an excellent MMPs inhibiting action, it is useful as an agent for treating or preventing diseases which can be expected to be improved by the present action, for example, rheumatoid arthritis, osteoarthritis, osteoporosis, periodontal disease, ectopic angiogenesis, multiple sclerosis, metastasis of tumor, cornea ulcer and the like.

When the dithiazole compound (I) of the present invention is administered for the medical purpose, an administration route is not particularly limited, and the compound can be administered by any method, for example, orally, parenterally or locally. A dose is appropriately adjusted depending on subject (mammal, particularly human), an age, sex, individual difference, symptom and the like, being not particularly limited. For example, a dose of 0.1 to 500 mg/kg, preferably 0.5 to 200 mg/kg of the dithiazole compound (I) of the present invention can be administered orally or parenterally in a single dose or several doses per day.

The dithiazole compound (I) of the present invention can be administered in various preparation forms. An amount of an active ingredient in a preparation is not particularly limited, but is usually 0.01% to 70% by weight, preferably 0.1 to 50% by weight.

A preparation is prepared using a normal preparation carrier by a conventional method and, if necessary, pharmacologically acceptable additives may be added thereto.

That is, when an oral solid preparation is prepared, an excipient and, further, if necessary, a binder, a disintegrating agent, a lubricant, a colorant, a corrigent and the like are added to an active component to form tablets, coated tablets, granules, powders, capsules or the like by a conventional method.

As the excipient, for example, lactose, corn starch, sucrose, glucose, sorbit, crystalline cellulose, silicon dioxide, calcium phosphate, glycine and the like can be used. As the binder, for example, polyvinyl alcohol, polyvinyl ether, ethyl cellulose, methyl cellulose, gum arabic, tragacanth, gelatin, shellac, hydroxypropyl cellulose, hydroxypropyl starch, polyvinylpyrrolidone and the like can be used. As the disintegrating agent, for example, starch, agar, gelatin powder, crystalline cellulose, calcium carbonate, sodium hydrogencarbonate, calcium citrate, sodium citrate, dextrin, pectin, alginic acid and the like can be used. As the lubricant, for example, magnesium stearate, sodium laurate, talc, polyethylene glycol, silica, hydrogenated vegetable oil and the like can be used. As the colorant, those permitted to be added to pharmaceutical preparations can be used. As the corrigent, cocoa powder, menthol, aromatic acid, mentha oil, borneol and cinnamon powder can be used. If necessary, tablets, granules and the like can be appropriately coated with a sugar coating, a gelatin coating or the like.

When an oral liquid formulation is prepared, a corrigent, a colorant, an emulsifying agent, a suspending agent, a diluent and the like may be added to an active ingredient to form an aqueous suspension, an elixir, a syrup or the like.

An injection (intramuscular, intraperitoneal, intra-articular, subcutaneous, intraveneous injections or the like) can be a sterile aqueous or non-aqueous solution, suspension and emulsion. If necessary, auxiliary agents such as an antiseptic, a wetting agent, an emulsifying agent, a dispersing agent, a stabilizer and a solubilizer may be contained therein. An injection is usually sterilized by filtration (bacteria-retaining filter etc.), incorporation of a germicide or γ-ray irradiation. Alternatively, after these treatments, it is converted into a solid composition by freeze-drying or the like, which is used by adding sterile water or sterile injectable diluent thereinto just before use.

The compound may be also administered parenterally as a suppository.

Further, the dithiazole compound (I) of the present invention may be incorporated into a skin external composition, which is particularly effective as an anti-aging cosmetic for the purpose of improving or preventing skin aging such as wrinkles, slacks and dullness of a skin. The "anti-aging cosmetic" in the present invention broadly means a cosmetic for preventing or improving aging, in particular, aging of a skin.

When the present compound is used in a skin external composition, an amount of the dithiazole compound (I) to be incorporated is 0.00001 to 10% by weight, preferably 0.0001 to 5% by weight in a total amount of the composition. When the amount is less than 0.00001% by weight, the effect is not sufficiently exerted. On the other hand, when the amount exceeds 10% by weight, considerable improvement in the effect is not recognized, and formulation becomes difficult in some cases.

Into the skin external composition of the present invention, if necessary, can be appropriately incorporated other ingredients which are usually used in an external composition such as a cosmetic or pharmaceutical product in addition to the dithiazole compound (I) as an active ingredient, within a range that the effect of the present invention is not deteriorated. For example, a whitening agent, a humectant, an antioxidant, an oily ingredient, an ultraviolet absorbing agent, a surfactant, a thickener, an alcohol, a powder ingredient, a coloring agent, an aqueous ingredient, water, various skin nutrients and the like can be incorporated therein.

Further, a metal sequesting agent such as disodium edatate, trisodium edatate, sodium citrate, sodium polyphosphate, sodium metaphosphate, or gluconic acid; a drug such as caffeine, tannin, verapamil, tranexamic acid and a derivative thereof, a glycyrrhiza extract, glove lysine, hot water extract of a fruit of Chinese quince, various crude drugs, tocopherol acetate, or glycyrrhizic acid and a derivative thereof and a salt thereof; a whitening agent such as vitamin C, magnesium ascorbylphosphate, ascorbyl glucoside, arbutin or kojic acid; a sugar such as glucose, fructose, mannose, sucrose or trehalose; a vitamin A derivative such as retinoic acid, retinol, retinol acetate or retinol palmitate; and the like may be appropriately incorporated therein.

The form of the skin external composition is not particularly limited, and can be arbitrary forms such as solution system, solubilized system, emulsified system, powder dispersed system, water-oil biphase system, water-oil-powder triphase system, solid ointment, gel, aerosol, mousse and the like. In addition, its use form is also arbitrary, and may be a base cosmetic such as a lotion, an emulsion, a cream, a pack, an essence or the like, a makeup cosmetic such as foundation or the like, a hair cosmetic, a fragrance cosmetic, a bath preparation or the like, but it is not limited thereto.

EXAMPLE

The present invention will be explained by way of embodiments below.

MMPs Inhibition Test (a) Preparation of Sample Solution

A test material was dissolved in dimethyl sulfoxide (DMSO) to the concentration of 10 mM, to prepare a stock solution. The stock solution was diluted with a measuring buffer (0.05M tris at pH 7.5 containing 0.2M NaCl and 5 mM $CaCl_2$) to adjust the concentration to 100 μM, which was used as a sample solution. As a control solution, a solution containing no test material was similarly prepared.

(b) Gelatinase Group MMPs Inhibition Test

As a gelatinase group enzyme, MMP-9 (crude enzyme solution derived from a mouse skin) was used. The test was performed according to a gelatin zymography method ("Bio-antioxidant provitamin C", Nobuhiko Miwa ed., p.76, 1999, Fragrance Journal, Tokyo).

That is, a gel containing gelatin in which a predetermined amount of the crude enzyme solution had been subjected to electrophoresis in advance, was incubated overnight with a sample solution or a control solution. After the gel was stained, the appearing band corresponding to MMP-9 was evaluated by a decrease when its size compared with that of a band of control solution. Evaluation criteria was as follows:

⊚: The band disappeared.

◯: The band was slightly confirmed.

Δ: The band became narrower than control.

×: Unchanged.

(c) Result

Using the following dithiazole compounds as a test material, the test was performed. As clearly from Table 1, dithiazole compounds of the present invention inhibited MMPs activity.

Compound 1:
2-{Benzyl[(4-methoxyphenyl)sulfonyl]amino}-N-(3-thioxo-3H-1,2,4-dithiazol-5-yl)acetoamide Compound 2:
2-{4-[(3,7-Dimethyl-2,6-octadienyl)oxy]phenyl}-N-(3-thioxo-3H-1,2,4-dithiazol-5-yl)acetoamide Compound 5:
2-{4-[(4-Fluorobenzyl)oxy]phenyl}-N-(3-thioxo-3H-1,2,4-dithiazol-5-yl)acetoamide Compound 7:
2-{2-[(4-Fluorobenzyl)oxy]phenyl}-N-(3-thioxo-3H-1,2,4-dithiazol-5-yl)acetoamide Compound 8:
2-{3-[(4-Fluorobenzyl)oxy]phenyl}-N-(3-thioxo-3H-1,2,4-dithiazol-5-yl)acetoamide Compound 9:
2-{3,5-Bis[(4-fluorobenzyl)oxy]phenyl}-N-(3-thioxo-3H-1,2,4-dithiazol-5-yl)acetoamide Compound 12:
2-{4-[(4-Fluorobenzyl)oxy]phenyl}-3-methyl-N-(3-thioxo-3H-1,2,4-dithiazol-5-yl) butanamide

TABLE 1

| Test Material | MMPs Inhibition |
| --- | --- |
| Compound 1 | ○ |
| Compound 2 | ○ |
| Compound 5 | ○ |
| Compound 7 | ○ |
| Compound 8 | ○ |
| Compound 9 | ○ |
| Compound 12 | ◎ |

In the following, Examples and Compounding Examples of the present invention will be explained, and the present invention is not limited thereto.

Example 1

2-{Benzyl[(4-methoxyphenyl)sulfonyl]amino}-N-(3-thioxo-3H-1,2,4-dithiazol-5-yl) acetoamide (Compound 1)

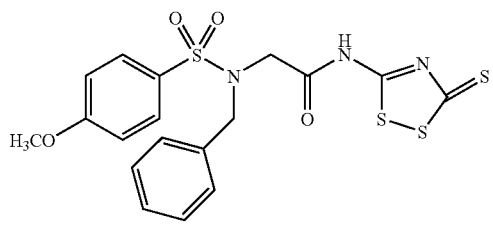

(a) Benzylamine hydrochloride (21.5 g, 150.0 mmol) was dissolved in chloroform (114 ml) and cooled to 0° C. Triethylamine (20.9 ml, 150.0 mmol) and 4-methoxybenzenesulfonyl chloride (10.3 g, 50.0 mmol) were added to the solution, and the mixture was reacted for 2 hours at room temperature, followed by for 1 hour at 60° C. After standing to cool, the reaction mixture was washed with 4N hydrochloric acid (200 ml×3), water (100 ml×2) and saturated brine (50 ml) successively. Then, the solvent was dried over sodium sulfate and evaporated out, to give N-benzyl-4-methoxybenzenesulfonamide (13.25 g, 96%).

$^1$H-NMR(CDCl$_3$) δ 7.80(2H, d), 7.30-7.18(5H, m), 6.97 (2H, d), 4.63(1H, t), 4.11(2H, d), 3.88(3H, s).

(b) A solution of N-benzyl-4-methoxybenzenesulfonamide (15.00 g, 36.06 mmol) in tetrahydrofuran (90 ml) was added to a suspension of sodium hydride (60% oil suspension 1.47 g, 36.78 mmol) in tetrahydrofuran (90 ml) and stirred for 50 minutes at room temperature. Then the suspension, with ethyl bromoacetate (6.00 ml, 54.09 mmol) added thereto, was stirred for 14 hours at room temperature. After the reaction, the mixture, with water (100 ml) added thereto, was extracted with ethyl acetate (100 ml×3). The organic layer was dried over sodium sulfate, and then the solvent was evaporated out. The residue was purified by silica gel column chromatography (20% ethyl acetate/hexane), to give ethyl 2-{benzyl[(4-methoxyphenyl)sulfonyl] amino}acetate (18.82 g, 96%).

$^1$H-NMR(CDCl$_3$) δ 7.83(2H, d), 7.33-7.24(5H, m), 6.98 (2H, d), 4.48(2H, s), 4.01(2H, q), 3.90(2H, s), 3.88(3H, s), 1.15(3H, t).

(c) Ethyl 2-{benzyl[(4-methoxyphenyl)sulfonyl] amino}acetate (11.62 g, 31.97 mmol) was dissolved in ethanol (100 ml), and 1N sodium hydroxide (100 ml) was added thereto. After being reacted for 16 hours at room temperature, the solvent was evaporated out. 3N hydrochloric acid (150 ml) was added to the residue and the water phase was extracted with ethyl acetate (200 ml×2). The organic layer was washed with saturated brine, and then dried over sodium sulfate. The solvent was evaporated out and the residue was purified by silica gel column chromatography (chloroform:methanol=10:1), to give 2-{benzyl [(4-methoxyphenyl)sulfonyl]amino}acetic acid (10.57 g, 99%).

$^1$H-NMR(CDCl$_3$) δ 7.82(2H, d), 7.31-7.20(5H, m), 6.97 (2H, d), 4.46(2H, s), 3.92(2H, s), 3.87(3H, s).

(d) N-methylmorpholine (0.79 ml, 7.15 mmol), N-hydroxybenzotriazole (1.10 g, 7.15 mmol) and 1-ethyl-3-(3'-dimethylaminopropyl)carbodiimide hydrochloride (1.37 g, 7.15 mmol) are added to a solution of 2-{benzyl[(4-methoxyphenyl)sulfonyl]amino}acetic acid (2.00 g, 5.96 mmol) in N,N-dimethylformamide (20 ml) while being cooled with ice, and stirred for 1 hour. Then, the mixture, with 3-amino-1,2,4-dithiazole-5-thione (1.08 g, 7.15 mmol) added thereto, was stirred for 5 hours at room temperature. The reaction, with 1N hydrochloric acid added thereto, was extracted with ethyl acetate. The organic layer was washed with sodium bicarbonate water and saturated brine successively, dried over sodium sulfate anhydride, and concentrated. The residue was purified by silica gel column chromatography (3% methanol/chloroform), to give aimed 2-{benzyl[(4-methoxyphenyl)sulfonyl]amino}-N-(3-thioxo-3H-1,2,4-dithiazol-5-yl)acetoamide (Compound 1) (0.883 g, 32%).

$^1$H-NMR(DMSO-d$_6$) δ 7.80(2H, d), 7.31-7.25(5H, m), 7.10(2H, d), 4.42(2H, s), 4.14(2H, s), 3.85(3H, s).

Example 2

2-{4-[(3,7-Dimethyl-2,6-octadienyl)oxy]phenyl}-N-(3-thioxo-3H-1,2,4-dithiazol-5-yl)acetoamide (Compound 2)

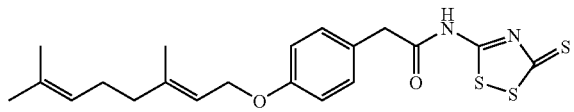

(a) Methyl 4-hydroxyphenylacetate (6.00 g, 36.11 mmol) was dissolved in acetone (90 ml), and then potassium carbonate (9.98 g, 72.22 mmol) and geranyl bromide(14.34 ml, 72.22 mmol) were added thereto. After being refluxed for 4 hours, the mixture, with water added thereto, was extracted with ethyl acetate. The organic layer was washed with saturated ammonium chloride water and saturated brine successively, and dried over MgSO$_4$. The solvent was evaporated out and the obtained residue was purified by silica gel column chromatography (5% ethyl acetate/hexane), to give methyl 2-{4-[(3,7-dimethyl-2,6-octadienyl) oxy]phenyl}acetate (10.07 g, 92%).

$^1$H-NMR(CDCl$_3$) δ 7.18(2H, d), 6.87(2H, d), 5.48(1H, t), 5.09(1H, t), 4.51(2H, d), 3.68(3H, s), 3.56(2H, s), 2.13-2.06 (4H, m), 1.72(3H, s), 1.68(3H, s), 1.59(3H, s).

(b) 1N potassium hydroxide (46 ml) was added to a solution of methyl 2-{4-[(3,7-dimethy-2,6-octadienyl)oxy]phenyl}acetate (9.46 g, 31.28 mmol) in methanol (70 ml) and refluxed for 1 hour. The mixture, with 3N hydrochloric acid (50 ml) added thereto, was extracted with ethyl acetate. The organic layer was washed with saturated brine, dried over MgSO$_4$, and then concentrated. The residue was purified by recrystallization (ethyl acetate/hexane), to give 2-{4-[(3,7-dimethyl-2,6-octadienyl)oxy]phenyl}acetic acid (5.50 g, 61%).

$^1$H-NMR(CDCl$_3$) δ 7.18(2H, d), 6.88(2H, d), 5.48(1H, t), 5.09(1H, t), 4.51 (2H, d), 3.58(2H, s), 2.13-2.06(4H, m), 1.72(3H, s), 1.68(3H, s), 1.60(3H, s).

(c) 2-{4-[(3,7-Dimethyl-2,6-octadienyl)oxy]phenyl}acetic acid (1.00 g, 3.47 mmol) was dissolved in tetrahydrofuran (12 ml), and 1,1'-carbonyldiimidazole (0.68 g, 4.16 mmol) was added thereto. The mixture was stirred for 1 hour at room temperature, and then 3-amino-1,2,4-dithiazole-5-thione (0.42 g, 2.70 mmol) was added thereto. After being stirred for 3 hours at room temperature, the mixture, with water added thereto, was extracted with ethyl acetate. The organic layer was washed with saturated brine, dried over MgSO$_4$, and then concentrated. The obtained residue was purified by silica gel chromatography (chloroform), to give 2-{4-[(3,7-dimethyl-2,6-octadienyl)oxy]phenyl}-N-(3thioxo-3H-1,2,4-dithiazol-5-yl)acetoamide (Compound 2) (0.187 g, 18%).

$^1$H-NMR(CDCl$_3$) δ 7.15(2H, d), 6.87(2H, d), 5.48(1H, t), 5.09(1H, t), 4.51(2H, d), 3.96(2H, s), 2.13-2.06(4H, m), 1.73(3H, s), 1.68(3H, s), 1.61(3H, s).

Example 3

3-{4-[(3,7-Dimethyl-2,6-octadienyl)oxy]phenyl}-N-(3-thioxo-3H-1,2,4-dithiazol-5-yl) propanamide (Compound 3)

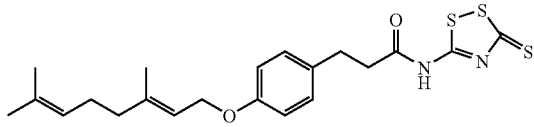

(a) Methyl 3-(4-hydroxyphenyl)propionate (5.01 g, 27.80 mmol) was dissolved in acetone (55 ml), and potassium carbonate (7.69 g, 55.60 mmol) and geranyl bromide (12.1 ml, 55.60 mmol) were added thereto. After being refluxed for 3 hours, the mixture, with water added thereto, was extracted with ethyl acetate. The organic layer was washed with saturated ammonium chloride water and saturated brine successively and dried over MgSO$_4$, and the solvent was evaporated out.

(b) The obtained residue was dissolved in a mixture of methanol (100 ml) and tetrahydrofuran (20 ml), and then 1N potassium hydroxide (50 ml) was added thereto. After being refluxed for 2 hours, the mixture, with 3N hydrochloric acid (50 ml) added thereto, was extracted with ethyl acetate. The organic layer was washed with saturated brine, dried over MgSO$_4$, and then concentrated. The residue was washed with hexane, to give 3-{4-[(3,7-dimethyl-2,6-octadienyl)oxy]phenyl}propionic acid (3.84 g, 46%).

$^1$H-NMR(CDCl$_3$) δ 7.11(2H, d), 6.84(2H, d), 5.48(1H, t), 5.09(1H, t), 4.51 (2H, d), 2.90(2H, t), 2.64(2H, t), 2.13-2.06 (4H, m), 1.72(3H, s), 1.68(3H, s), 1.60(3H, s).

(c) 3-{4-[(3,7-Dimethyl-2,6-octadienyl)oxy]phenyl}propionic acid (1.00 g, 3.31 mmol) was dissolved in tetrahydrofuran (11 ml), and 1,1'-carbonyldiimidazole (0.643 g, 3.97 mmol) was added thereto. The imidazole mixture was stirred for 1 hour at 0° C. Sodium hydride (60% oil suspension 0.132 g, 3.31 mmol) was suspended in tetrahydrofuran (11 ml), and 3-amino-1,2,4-dithiazole-5-thione (0.497 g, 3.31 mmol) was added thereto. After being stirred for 30 minutes at 0° C., the reaction mixture, with the imidazole mixture added thereto, was stirred for 2 hours at 0° C. The mixture, with water added thereto, was extracted with ethyl acetate. The organic layer was washed with saturated brine, dried over MgSO$_4$, and then concentrated. The obtained residue was purified by silica gel column chromatography (chloroform), to give 3-{4-[(3,7-dimethyl-2,6-octadienyl)oxy]phenyl}-N-(3-thioxo-3H-1,2,4-dithiazol-5-yl)propanamide (Compound 3) (0.847 g, 59%).

$^1$H-NMR(CDCl$_3$) δ 11.54(1H, brs), 7.07(2H, d), 6.80(2H, d), 5.47(1H, t), 5.08(1H, t), 4.48(2H, d), 3.05(2H,t), 2.95 (2H, s), 2.13-2.06(4H, m), 1.72(3H, s), 1.67(3H, s), 1.60(3H, s).

Example 4

3-{4-[(4-Fluorobenzyl)phenyl}-N-(3-thioxo-3H-1,2,4-dithiazol-5-yl)acrylamide (Compound 4)

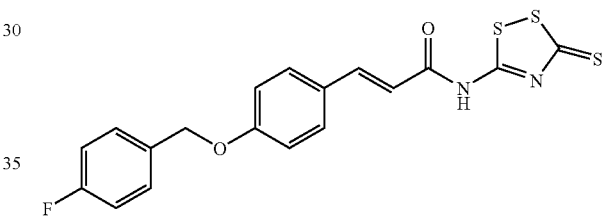

(a) Trans-4-hydroxycinnamic acid (5.00 g, 30.46 mmol) was dissolved in ethanol (60 ml), and sulfuric acid (1.6 ml) was added thereto. The mixture was refluxed for 5 hours and then the solvent was evaporated out. The residue was diluted with water, neutralized with sodium hydrogencarbonate, and then extracted with ethyl acetate. The organic layer was washed with saturated brine and dried over MgSO$_4$, and then the solvent was evaporated out.

(b) The obtained residue was dissolved in acetone (60 ml), and potassium carbonate (8.80 g, 63.66 mmol) and 4-fluorobenzyl chloride (7.61 ml, 63.66 mmol) were added thereto. After being refluxed for 6 hours, the mixture, with water added thereto, was extracted with ethyl acetate. The organic layer was washed with saturated brine and dried over MgSO$_4$, and then the solvent was evaporated out.

(c) The obtained residue was dissolved in a mixture of methanol (30 ml) and tetrahydrofuran (30 ml), and 1N potassium hydroxide (30 ml) was added thereto. After being refluxed for 2 hours, the mixture, with 3N hydrochloric acid (30 ml) added thereto, was extracted with ethyl acetate. The organic layer was washed with saturated brine, dried over MgSO$_4$, and then concentrated. The residue was washed with ethyl acetate, to give 3-{4-[(4-fluorobenzyl)oxy]phenyl}acrylic acid (8.03 g, 96%).

$^1$H-NMR(DMSO-d$_6$) δ 12.17(1H, brs), 7.62(2H, d), 7.56-7.48(3H, m), 7.24-7.18(2H, m), 7.04(2H, d), 6.38(2H, d), 5.14(2H,s).

(d) 3-{4-[(4-Fluorobenzyl)oxy]phenyl}acrylic acid (1.00 g, 3.67 mmol) was dissolved in tetrahydrofuran (11 ml), and 1,1'-carbonyldiimidazole (0.714 g, 4.40 mmol) was added thereto. The imidazole mixture was stirred for 1 hour at room temperature. Sodium hydride (60% oil suspension 0.147 g, 3.67 mmol) was suspended in tetrahydrofuran (11 ml), and 3-amino-1,2,4-dithiazole-5-thione (0.552 g, 3.67 mmol) was added thereto. After being stirred for 30 minutes at 0° C., the reaction mixture, with the imidazole mixture added thereto, was stirred for 2 hours at room temperature. The mixture, with water added thereto, was extracted with ethyl acetate. The organic layer was washed with saturated brine, dried over MgSO$_4$, and then concentrated. The obtained residue was purified by silica gel column chromatography (chloroform), to give 3-{4-[(4-fluorobenzyl)oxy]phenyl}-N-(3-thioxo-3H-1,2,4-dithiazol-5-yl)acrylamide (Compound 4) (0.139 g, 9%).

$^1$H-NMR(DMSO-d$_6$) δ 7.86(1H, d), 7.67(2H, d), 7.54-7.49(2H, m), 7.24-7.20(2H, m), 7.10(2H, d), 6.73(1H, d), 5.17(2H,s).

Example 5

2-{4-[(4-Fluorobenzyl)oxy]phenyl}-N-(3-thioxo-3H-1,2,4-dithiazol-5-yl)acetoamide (Compound 5)

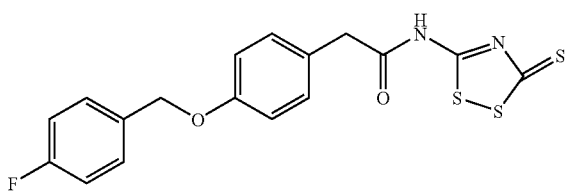

(a) Methyl 4-hydroxyphenylacetate (4.00 g, 24.07 mmol) was dissolved in acetone (60 ml), and potassium carbonate (6.65 g, 48.14 mmol) and 4-fluorobenzyl chloride (5.76 ml, 48.14 mmol) were added thereto. After being refluxed for 22 hours, the mixture, with water added thereto, was extracted with ethyl acetate. The organic layer was washed with saturated brine and dried over MgSO$_4$, and then the solvent was evaporated out.

(b) The obtained residue was dissolved in a mixture of methanol (30 ml) and tetrahydrofuran (30 ml), and 1N potassium hydroxide (40 ml) was added thereto. After being refluxed for 3 hours, the mixture, with 3N hydrochloric acid (40 ml) added thereto, was extracted with ethyl acetate. The organic layer was washed with saturated brine, dried over MgSO$_4$, and then concentrated. The residue was purified by recrystallization (ethyl acetate/hexane), to give 2-{4-[(4-fluorobenzyl)oxy]phenyl}acetic acid (5.65 g, 90%).

$^1$H-NMR(CDCl$_3$) δ 7.39(2H, m), 7.20(2H, d), 7.06(2H, m), 6.92(2H, d), 5.00(2H, s), 3.59(2H,s).

(c) 2-{4-[(4-Fluorobenzyl)oxy]phenyl}acetic acid (1.00 g, 3.84 mmol) was dissolved in tetrahydrofuran (10 ml), and 1,1'-carbonyldiimidazole (0.748 g, 4.61 mmol) was added thereto. The imidazole mixture was stirred for 1 hour at room temperature. Sodium hydride (60% oil suspension 0.131 g, 3.27 mmol) was suspended in tetrahydrofuran (8 ml), and 3-amino-1,2,4-dithiazole-5-thione (0.491 g, 3.27 mmol) was added thereto. After being stirred for 30 minutes at 0° C., the reaction mixture, with the imidazole mixture added thereto, was stirred for 3 hours at room temperature. The mixture, with water added thereto, was extracted with ethyl acetate. The organic layer was washed with saturated brine, dried over MgSO$_4$, and then concentrated. The obtained residue was purified by silica gel column chromatography (chloroform), to give 2-{4-[(4-fluorobenzyl)oxy]phenyl}-N-(3-thioxo-3H-1,2,4-dithiazol-5-yl)acetoamide (Compound 5) (0.431 g, 29%).

$^1$H-NMR(DMSO-d$_6$) δ 7.47(2H, m), 7.25-7.17(4H, m), 6.97(2H, d), 5.06(2H, s), 3.83(2H,s).

Example 6

2-[4-(Octyloxy)phenyl]-N-(3-thioxo-3H-1,2,4-dithiazol-5-yl)acetoamide (Compound 6)

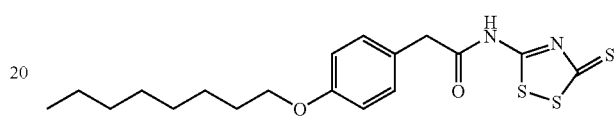

(a) Methyl 4-hydroxyphenylacetate (4.00 g, 24.07 mmol) was dissolved in acetone (48 ml), and potassium carbonate (6.65 g, 48.14 mmol) and 1-bromooctane (8.38 ml, 48.14 mmol) were added thereto. After being stirred for 21 hours, the mixture, with water added thereto, was extracted with ethyl acetate. The organic layer was washed with saturated brine and dried over MgSO$_4$, and then the solvent was evaporated out.

(b) The obtained residue was dissolved in a mixture of methanol (30 ml) and tetrahydrofuran (30 ml), and 1N potassium hydroxide (40 ml) was added thereto. After being refluxed for 2 hours, the mixture, with 3N hydrochloric acid (50 ml) added thereto, was extracted with ethyl acetate. The organic layer was washed with saturated brine, dried over MgSO$_4$, and then concentrated. The residue was washed with hexane, to give 2-[4-(octyloxy)phenyl]acetic acid (4.84 g, 76%).

$^1$H-NMR(CDCl$_3$) δ 7.18(2H, d), 6.85(2H, d), 3.93(2H, t), 3.57(2H, s), 1.80-1.73(2H, m), 1.46-1.28(10H, m), 0.89(3H, t).

(c) 2-[4-(Octyloxy)phenyl]acetic acid (0.900 g, 3.40 mmol) was dissolved in tetrahydrofuran (11 ml), and 1,1'-carbonyldiimidazole (0.622 g, 4.09 mmol) was added thereto. The imidazole mixture was stirred for 1 hour at 0° C. Sodium hydride (60% oil suspension 0.136 g, 3.40 mmol) was suspended in tetrahydrofuran (11 ml), and 3-amino-1,2,4-dithiazole-5-thione (0.511 g, 3.40 mmol) was added thereto. After being stirred for 30 minutes at 0° C., the reaction mixture, with the imidazole mixture added thereto, was stirred for 3 hours at 0° C. The mixture, with water added thereto, was extracted with ethyl acetate. The organic layer was washed with saturated brine, dried over MgSO$_4$, and then concentrated. The obtained residue was purified by silica gel column chromatography (chloroform), to give 2-[4-(octyloxy)phenyl]-N-(3-thioxo-3H-1,2,4-dithiazol-5-yl)acetoamide (Compound 6) (0.290 g, 21%).

$^1$H-NMR(DMSO-d$_6$) δ 13.86(1H, brs), 7.22(2H, d), 6.88 (2H, d), 3.94(2H, t), 3.83(2H, s), 1.72-1.65(2H, m), 1.41-1.26(10H, m), 0.86(3H, t).

Example 7

2-{2-[(4-Fluorobenzyl)oxy]phenyl}-N-(3-thioxo-3H-1,2,4-dithiazol-5-yl)acetoamide (Compound 7)

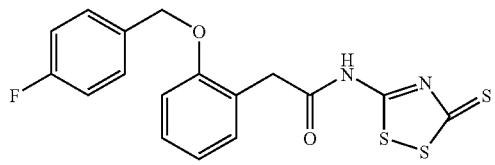

(a) 2-Hydroxyphenylacetic acid (5.19 g, 34.11 mmol) was dissolved in ethanol (68 ml), and sulfuric acid (1.8 ml) was added thereto. After being refluxed for 14 hours, the solvent was evaporated out. The residue was diluted with water, neutralized with sodium hydrogencarbonate, and then extracted with ethyl acetate. The organic layer was washed with saturated brine and dried over $MgSO_4$, and then the solvent was evaporated out.

(b) The obtained residue was dissolved in acetone (69 ml), and potassium carbonate (9.59 g, 69.37 mmol) and 4-fluorobenzyl chloride (8.29 ml, 69.37 mmol) were added thereto. After being refluxed for 19 hours, the mixture, with water added thereto, was extracted with ethyl acetate. The organic layer was washed with saturated brine and dried over $MgSO_4$, and then the solvent was evaporated out.

(c) The obtained residue was dissolved in a mixture of methanol (30 ml) and tetrahydrofuran (30 ml), and 1N potassium hydroxide (30 ml) was added thereto. After being refluxed for 2 hours, the mixture, with 3N hydrochloric acid (30 ml) added thereto, was extracted with ethyl acetate. The organic layer was washed with saturated brine, dried over $MgSO_4$, and then concentrated. The residue was purified by silica gel column chromatography, to give 2-{2-[(4-fluorobenzyl)oxy]phenyl}acetic acid (3.45 g, 39%). $^1$H-NMR (CDCl$_3$) δ 7.33(2H, m), 7.27-7.20(2H, m), 7.01-6.90(4H, m), 5.01(2H, s), 3.69(2H, s).

(d) 2-{2-[(4-Fluorobenzyl)oxy]phenyl}acetic acid (1.04 g, 3.99 mmol) was dissolved in tetrahydrofuran (13 ml), and 1,1'-carbonyidiimidazole (0.777 g, 4.79 mmol) was added thereto. The imidazole mixture was stirred for 1 hour at room temperature. Sodium hydride (60% oil suspension 0.160 g, 3.99 mmol) was suspended in tetrahydrofuran (13 ml), and 3-amino-1,2,4-dithiazole-5-thione (0.601 g, 3.99 mmol) was added thereto. After being stirred for 30 minutes at 0° C., the reaction mixture, with the imidazole mixture added thereto, was stirred for 16 hours at room temperature. The reaction mixture, with water added thereto, was extracted with ethyl acetate. The organic layer was washed with saturated brine, dried over $MgSO_4$, and then concentrated. The obtained residue was purified by silica gel chromatography (chloroform), to give 2-{2-[(4-fluorobenzyl)oxy]phenyl}-N-(3-thioxo-3H-1,2,4-dithiazol-5-yl)acetoamide (Compound 7) (0.523 g, 33%).

$^1$H-NMR(CDCl$_3$) δ 7.41-7.34(3H, m), 7.27-7.25(1H, m), 7.10-7.01(4H, m), 5.10(2H, s), 3.89(2H, s).

Example 8

2-{3-[(4-Fluorobenzyl)oxy]phenyl}-N-(3-thioxo-3H-1,2,4-dithiazol-5-yl)acetoamide (Compound 8)

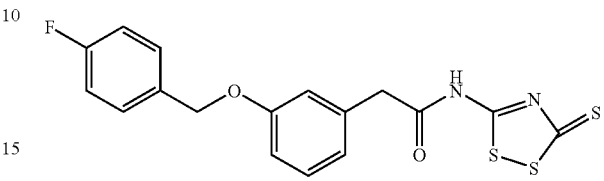

(a) 3-Hydroxyphenylacetic acid (5.24 g, 34.46 mmol) was dissolved in ethanol (68 ml), and sulfuric acid (1.8 ml) was added thereto. The mixture was refluxed for 14 hours, and then the solvent was evaporated out. The residue was diluted with water, neutralized with sodium hydrogencarbonate, and then extracted with ethyl acetate. The organic layer was washed with saturated brine and dried over $MgSO_4$, and then the solvent was evaporated out.

(b) The obtained residue was dissolved in acetone (69 ml), and potassium carbonate (9.52 g, 68.88 mmol) and 4-fluorobenzyl chloride (8.23 ml, 68.88 mmol) were added thereto. After being refluxed for 15 hours, the mixture, with water added thereto, was extracted with ethyl acetate. The organic layer was washed with saturated brine and dried over $MgSO_4$, and then the solvent was evaporated out.

(c) The obtained residue was dissolved in a mixture of methanol (30 ml) and tetrahydrofuran (30 ml), and 1N potassium hydroxide (30 ml) was added thereto. After being refluxed for 2 hours, the mixture, with 3N hydrochloric acid (30 ml) added thereto, was extracted with ethyl acetate. The organic layer was washed with saturated brine, dried over $MgSO_4$, and then concentrated. The residue was washed with hexane, to give 2-{3-[(4-fluorobenzyl)oxy]phenyl}acetic acid (8.09 g, 90%).

$^1$H-NMR(CDCl$_3$) δ 7.41-7.37(2H, m), 7.25(2H, t), 7.09-7.03(2H, m), 6.91-6.87(2H, m), 5.01(2H, s), 3.62(2H, s).

(d) 2-{3-[(4-Fluorobenzyl)oxy]phenyl}acetic acid (1.00 g, 3.84 mmol) was dissolved in tetrahydrofuran (13 ml), and 1,1'-carbonyldiimidazole (0.748 g, 4.61 mmol) was added thereto. The imidazole mixture was stirred for 1 hour at 0° C. Sodium hydride (60% oil suspension 0.154 g, 3.84 mmol) was suspended in tetrahydrofuran (13 ml), and 3-amino-1,2,4-dithiazole-5-thione (0.577 g, 3.84 mmol) was added thereto. After being stirred for 30 minutes at 0° C., the reaction mixture, with the imidazole mixture added thereto, was stirred for 13 hours at room temperature. The mixture, with water added thereto, was extracted with ethyl acetate. The organic layer was washed with saturated brine, dried over $MgSO_4$, and then concentrated. The obtained residue was purified by silica gel column chromatography (chloroform), to give 2-{3-[(4-fluorobenzyl)oxy]phenyl}-N-(3-thioxo-3H-1,2,4-dithiazol-5-yl)acetoamide (Compound 8) (0.097 g, 6%).

$^1$H-NMR(DMSO-d$_6$) δ 7.52-7.48(2H, m), 7.29-718(3H, m), 7.00-6.90(3H, m), 5.08(2H, s), 3.89(2H, s).

Example 9

2-{3,5-Bis[(4-fluorobenzyl)oxy]phenyl}-N-(3-thioxo-3H-1,2,4-dithiazol-5-yl)acetoamide (Compound 9)

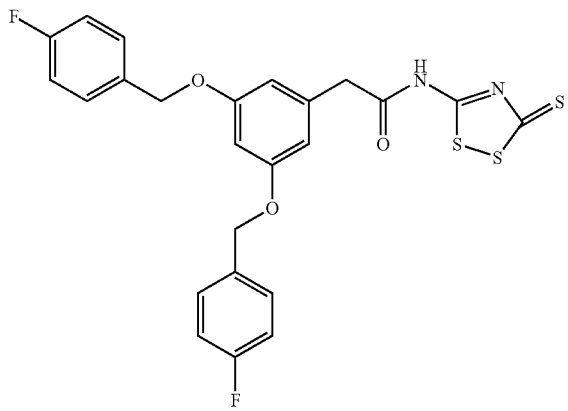

(a) Methyl 3,5-dihydroxyphenylacetate (2.00 g, 10.98 mmol) was dissolved in acetone (22 ml), and potassium carbonate (4.55 g, 32.94 mmol) and 4-fluorobenzyl chloride (3.94 ml, 32.94 mmol) were added thereto. After being refluxed for 24 hours, the mixture, with water added thereto, was extracted with ethyl acetate. The organic layer was washed with saturated brine and dried over MgSO$_4$, and then the solvent was evaporated out.

(b) The obtained residue was dissolved in a mixture of methanol (40 ml) and tetrahydrofuran (40 ml), and 1N potassium hydroxide (20 ml) was added thereto. After being refluxed for 13 hours, the mixture was acidified with 3N hydrochloric acid, and then extracted with ethyl acetate. The organic layer was washed with saturated brine, dried over MgSO$_4$, and then concentrated. The residue was purified by recrystallization (ethyl acetate/hexane), to give 2-{3,5-bis[(4-fluorobenzyl)oxy]phenyl}acetic acid (2.66 g, 63%).

$^1$H-NMR(CDCl$_3$) δ 7.37(4H, dd), 7.06(4H, t), 6.54-6.50 (3H, m), 4.97(4H, s), 3.58(2H,s).

(c) 2-{3,5-Bis[(4-fluorobenzyl)oxy]phenyl}acetic acid (1.00 g, 2.60 mmol) was dissolved in tetrahydrofuran (9 ml), and 1,1'-carbonyldiimidazole (0.506 g, 3.12 mmol) was added thereto. The imidazole mixture was stirred for 1 hour at room temperature. Sodium hydride (60% oil suspension 0.104 g, 2.60 mmol) was suspended in tetrahydrofuran (9 ml), and 3-amino-1,2,4-dithiazole-5-thione (0.391 g, 2.60 mmol) was added thereto. After being stirred for 30 minutes at 0° C., the reaction mixture, with the imidazole mixture added thereto, was stirred for 7 hours at room temperature. The reaction mixture, with saturated ammonium chloride water added thereto, was extracted with ethyl acetate. The organic layer was washed with saturated sodium bicarbonate water and saturated brine successively, dried over MgSO$_4$, and then concentrated. The obtained residue was purified by silica gel column chromatography (chloroform), to give 2-{3,5-bis[(4-fluorobenzyl)oxy]phenyl}-N-(3-thioxo-3H-1,2,4-dithiazol-5-yl)acetoamide (Compound 9) (0.292 g, 22%).

$^1$H-NMR(DMSO-d$_6$) δ 7.46(4H, dd), 7.18(4H, t), 6.60 (3H, m), 5.10(2H, s), 3.89(2H,s).

Example 10

2-[3,4-Bis(octyloxy)phenyl]-N-(3-thioxo-3H-1,2,4-dithiazol-5-yl)acetoamide (Compound 10)

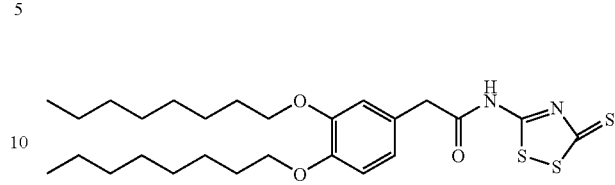

(a) 3,4-Dihydroxyphenylacetic acid (4.00 g, 23.79 mmol) was dissolved in methanol (48 ml), and sulfuric acid (1.3 ml) was added thereto. The mixture was refluxed for 13 hours, and then the solvent was evaporated out. The residue was diluted with water, neutralized with sodium hydrogencarbonate, and then extracted with ethyl acetate. The organic layer was washed with saturated brine and dried over MgSO$_4$, and then the solvent was evaporated out.

(b) The obtained residue (2.72 g) was dissolved in acetone (30 ml), and potassium carbonate (6.19 g, 44.79 mmol) and 1-bromooctane (7.79 ml, 44.79 mmol) were added thereto. After being refluxed for 54 hours, the mixture, with water added thereto, was extracted with ethyl acetate. The organic layer was washed with saturated brine and dried over MgSO$_4$, and then the solvent was evaporated out. The obtained residue was purified by silica gel column chromatography (hexane:chloroform=2:1), to give methyl 2-[3,4-bis(octyloxy)phenyl]acetate (3.94 g, 65%).

$^1$H-NMR(CDCl$_3$) δ 6.83-6.76(3H, m), 3.99-3.94(4H, m), 3.68(3H, s), 3.53(2H, s), 1.84-1.76(4H, m), 1.45-1.28(20H, m), 0.88(6H, t).

(c) Methyl 2-[3,4-bis(octyloxy)phenyl]acetate (3.94 g, 9.69 mmol) was dissolved in a mixture of methanol (30 ml) and tetrahydrofuran (30 ml), and 1N potassium hydroxide (19 ml) was added thereto. After being refluxed for 3 hours, the mixture was acidified with 3N hydrochloric acid, and then extracted with ethyl acetate. The organic layer was washed with saturated brine and dried over MgSO$_4$, and then the solvent was evaporated out, to give 2-[3,4-bis(octyloxy)phenyl]acetic acid (3.94 g, 89%).

$^1$H-NMR(CDCl$_3$) δ 6.83-6.77(3H, m), 3.97(4H, m), 3.56 (2H, s), 1.82-1.76(4H, m), 1.48-1.28(20H, m), 0.88(6H, t).

(d) 2-[3,4-Bis(octyloxy)phenyl]acetic acid (1.00 g, 2.55 mmol) was dissolved in tetrahydrofuran (8 ml), and 1,1'-carbonyldiimidazole (0.496 g, 3.06 mmol) was added thereto. The imidazole mixture was stirred for 1 hour at room temperature. Sodium hydride (60% oil suspension 0.102 g, 2.55 mmol) was suspended in tetrahydrofuran (8 ml), and 3-amino-1,2,4-dithiazole-5-thione (0.383 g, 2.55 mmol) was added thereto. After being stirred for 30 minutes at 0° C., the reaction mixture, with the imidazole mixture added thereto, was stirred for 16 hours at room temperature. The reaction mixture, with saturated ammonium chloride water added thereto, was extracted with ethyl acetate. The organic layer was washed with saturated sodium bicarbonate water and saturated brine successively, dried over MgSO$_4$, and then concentrated. The obtained residue was purified by silica gel column chromatography (chloroform), to give 2-[3,4-bis(octyloxy)phenyl]-N-(3-thioxo-3H-1,2,4-dithiazol-5-yl)acetoamide (Compound 10) (0.365 g, 33%).

$^1$H-NMR(DMSO-d$_6$) δ 6.93-6.88(2H, m), 6.81(1H, dd), 3.92(4H, m), 3.80(2H, s), 1.72-1.64(4H, m), 1.42-1.26(20H, m), 0.86(6H, t).

Example 11

2,2-Bis{4-[(4-fluorobenzyl)oxy]phenyl}-N-(3-thioxo-3H-1,2,4-dithiazol-5-yl)acetoamide (Compound 11)

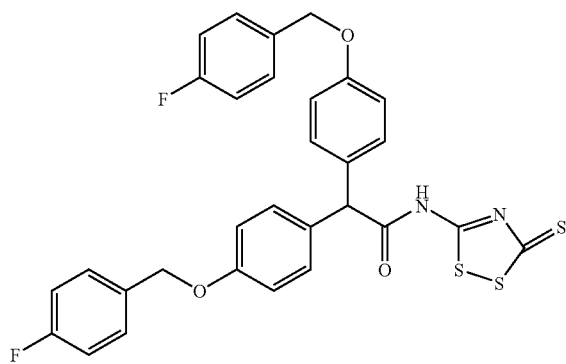

(a) Methyl 2,2-bis(4-hydroxyphenyl)acetate (3.00 g, 11.62 mmol) was dissolved in acetone (23 ml), and potassium carbonate (4.82 g, 34.85 mmol) and 4-fluorobenzyl chloride (4.16 ml, 34.85 mmol) were added thereto. After being refluxed for 40 hours, the mixture, with water added thereto, was extracted with ethyl acetate. The organic layer was washed with saturated brine and dried over $MgSO_4$, and then the solvent was evaporated out.

(b) The obtained residue was dissolved in a mixture of methanol (40 ml) and tetrahydrofuran (40 ml), and 1N potassium hydroxide (42 ml) was added thereto. After being refluxed for 15 hours, the mixture was acidified with 3N hydrochloric acid, and then extracted with ethyl acetate. The organic layer was washed with saturated brine and dried over $MgSO_4$, and then the solvent was evaporated out. The obtained residue was purified by recrystallization (ethyl acetate/hexane), to give 2,2-bis {4-[(4-fluorobenzyl)oxy]phenyl}acetic acid (4.38 g, 82%).

$^1$H-NMR($CDCl_3$) δ 7.38(4H, dd), 7.23(4H, d), 7.06(4H, t), 6.91(4H, d), 4.99(4H,s), 4.94(1H, s).

(c) 2,2-Bis{4-[(4-fluorobenzyl)oxy]phenyl}acetic acid (1.00 g, 2.17 mmol) was dissolved in tetrahydrofuran (7 ml), and 1,1'-carbonyldiimidazole (0.423 g, 2.61 mmol) was added thereto. The imidazole mixture was stirred for 1 hour at room temperature. Sodium hydride (60% oil suspension 0.087 g, 2.17 mmol) was suspended in tetrahydrofuran (7 ml), and 3-amino-1,2,4-dithiazole-5-thione (0.326 g, 2.17 mmol) was added thereto. After being stirred for 30 minutes at 0° C., the reaction mixture, with the imidazole mixture added thereto, was stirred for 17 hours at room temperature. The reaction mixture, with saturated ammonium chloride water added thereto, was extracted with ethyl acetate. The organic layer was washed with saturated sodium bicarbonate water and saturated brine successively, dried over $MgSO_4$, and then concentrated. The obtained residue was purified by silica gel column chromatography (chloroform), to give 2,2-bis{4-[(4-fluorobenzyl)oxy]phenyl}-N-(3-thioxo-3H-1,2,4-dithiazol-5-yl)acetoamide (Compound 11) (0.256 g, 20%).

$^1$H-NMR(DMSO-$d_6$) δ 7.47(4H, dd), 7.23-7.17(8H, m), 7.00(4H, d), 5.28(1H, s), 5.07(4H,s).

Example 12

2-{4-[(4-Fluorobenzyl)oxy]phenyl}-3-methyl-N-(3-thioxo-3H-1,2,4-dithiazol-5-yl)butanamide (Compound 12)

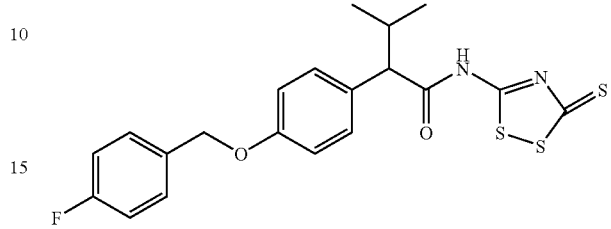

(a) 2-(p-Hydroxyphenyl)isovaleric acid (3.00 g, 15.45 mmol) was dissolved in methanol (30 ml), and sulfuric acid (0.82 ml) was added thereto. The mixture was refluxed for 13 hours, and then the solvent was evaporated out. The residue was diluted with water, neutralized with sodium hydrogencarbonate, and then extracted with ethyl acetate. The organic layer was washed with saturated brine and dried over $MgSO_4$, and then the solvent was evaporated out.

(b) The obtained residue was dissolved in acetone (31 ml), and potassium carbonate (4.27 g, 30.90 mmol) and 4-fluorobenzyl chloride (3.69 ml, 30.90 mmol) were added thereto. After being refluxed for 49 hours, the mixture, with water added thereto, was extracted with ethyl acetate. The organic layer was washed with saturated brine and dried over $MgSO_4$, and then the solvent was evaporated out.

(c) The obtained residue was dissolved in a mixture of methanol (40 ml) and tetrahydrofuran (40 ml), and 1N potassium hydroxide (40 ml) was added thereto. After being refluxed for 64 hours, the mixture was acidified with 3N hydrochloric acid, and then extracted with ethyl acetate. The organic layer was washed with saturated brine and dried over $MgSO_4$, and then the solvent was evaporated out. The obtained residue was purified by recrystallization (ethyl acetate/hexane), to give 2-{4-[(4-fluorobenzyl)oxy]phenyl}-3-methylbutanoic acid (4.23 g, 91%).

$^1$H-NMR($CDCl_3$) δ 7.38(2H, dd), 7.24(2H, d), 7.06(2H, t), 6.90(2H, d), 4.99(2H, s), 3.09(1H, d), 2.28(1H, m), 1.06(3H, d), 0.71(3H, d).

(d) 2-{4-[(4-Fluorobenzyl)oxy]phenyl}-3-methylbutanoic acid(1.00 g, 3.31 mmol) was dissolved in tetrahydrofuran (11 ml), and 1,1'-carbonyldiimidazole (0.644 g, 3.97 mmol) was added thereto. The imidazole mixture was stirred for 1 hour at room temperature. Sodium hydride (60% oil suspension 0.132 g, 3.31 mmol) was suspended in tetrahydrofuran (11 ml), and 3-amino-1,2,4-dithiazole-5-thione (0.497 g, 3.31 mmol) was added thereto. After being stirred for 30 minutes at 0° C., the reaction mixture, with the imidazole mixture added thereto, was stirred for 21 hours at room temperature. The reaction mixture, with saturated ammonium chloride water added thereto, was extracted with ethyl acetate. The organic layer was washed with saturated sodium bicarbonate water and saturated brine successively, dried over $MgSO_4$, and then concentrated. The obtained residue was purified by silica gel column chromatography (chloroform), to give 2-{4-[(4-fluorobenzyl)oxy]phenyl}-3-methyl-N-(3-thioxo-3H-1,2,4-dithiazol-5-yl)butanamide (Compound 12) (0.188 g, 13%).

$^1$H-NMR(DMSO-d$_6$) δ 7.38(2H, dd), 7.05(4H, m), 6.77 (2H, d), 4.91(2H, s), 3.68(1H, d), 2.40(1 H, m), 1.01(3H, d), 0.73(3H, d).

Example 13

2-{4-[(4-Fluorobenzyl)oxy]phenyl]-2-methyl-N-(3-thioxo-3H-1,2,4-dithiazol-5-yl) propanamide (Compound 13)

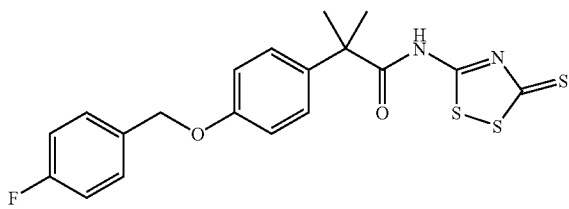

(a) Methyl 4-hydroxyphenylacetate (6.00 g, 36.11 mmol) was dissolved in acetone (72 ml), and potassium carbonate (7.49 g, 54.16 mmol) and 4-fluorobenzyl chloride (6.47 ml, 54.16 mmol) were added thereto. After being refluxed for 24 hours, the mixture, with water added thereto, was extracted with ethyl acetate. The organic layer was washed with saturated brine and dried over MgSO$_4$, and then the solvent was evaporated out. The obtained residue was purified by silica gel column chromatography (5% ethyl acetate/hexane), to give methyl 2-{4-[(4-fluorobenzyl)oxy]phenyl}acetate (9.18 g, 93%).

$^1$H-NMR(CDCl$_3$) δ 7.39(2H, dd), 7.19(2H, d), 7.06(2H, t), 6.91(2H, d), 5.00(2H,s), 3.68(3H, s), 3.56(2H, s).

(b) In argon atmosphere, sodium hydride (60% oil suspension 0.459 g, 11.48 mmol) was suspended in tetrahydrofuran (14 ml), and a solution of methyl 2-{4-[(4-fluorobenzyl) oxy]phenyl}acetate (1.50 g, 5.47 mmol) in tetrahydrofuran (13 ml) was added thereto while being cooled with ice. After being stirred for 1 hour at room temperature, the mixture, with methyl iodide (2.61 ml, 41.0 mmol) was added thereto, was stirred for 17 hours at 40° C. The mixture, with water added thereto, was extracted with ethyl acetate. The organic layer was washed with saturated brine and dried over MgSO$_4$, and then the solvent was evaporated out. The obtained residue was purified by silica gel column chromatography (2.5% ethyl acetate/hexane), to give methyl 2-{4-[(4-fluorobenzyl)oxy]phenyl}-2-methyl-propanoate (0.351 mg, 21%) and methyl 2-{4-[(4-fluorobenzyl)oxy]phenyl}propanoate (0.269 mg, 17%).

Methyl 2-{4-[(4-fluorobenzyl)oxy]phenyl}-2-methylpropanoate:
$^1$H-NMR(CDCl$_3$) δ 7.39(2H, dd), 7.27(2H, d), 7.06(2H, t), 6.91(2H, d), 5.00(2H, s), 3.64(3H,s), 1.56(6H, s).

Methyl 2-[4-(4-fluorobenzyl)oxy]phenyl}propanoate:
$^1$H-NMR(CDCl$_3$) δ 7.39(2H, dd), 7.22(2H, d), 7.06(2H, t), 6.92(2H, d), 4.99(2H, s), 3.67(1H, q), 3.65(3H, s), 1.47 (3H, d).

(c) Methyl 2-{4-[(4-fluorobenzyl)oxy]phenyl}-2-methyl-propanoate (0.351 mg, 1.16 mmol) was dissolved in a mixture of methanol (4 ml) and tetrahydrofuran (4 ml), and 1N potassium hydroxide (2 ml) was added thereto. After being refluxed for 5 hours, the mixture was acidified with 3N hydrochloric acid, and then extracted with ethyl acetate. The organic layer was washed with saturated brine and dried over MgSO$_4$, and then the solvent was evaporated out.

(d) The obtained residue was dissolved in tetrahydrofuran (3.3 ml), and 1,1'-carbonyldiimidazole (0.195 g, 1.20 mmol) was added thereto. The imidazole mixture was stirred for 1 hour at room temperature. Sodium hydride (60% oil suspension 0.048 g, 1.20 mmol) was suspended in tetrahydrofuran (3.3 ml), and 3-amino-1,2,4-dithiazole-5-thione (0.181 g, 1,20 mmol) was added thereto. After being stirred for 30 minutes at 0° C., he reaction mixture, with the imidazole mixture added thereto, was stirred for 16 hours at room temperature. The reaction mixture, with saturated ammonium chloride water added thereto, was extracted with ethyl acetate. The organic layer was washed with saturated sodium bicarbonate water and saturated brine successively, dried over MgSO$_4$, and then concentrated. The obtained residue was purified by silica gel column chromatography (chloroform:hexane=4:1), to give 2-{4-[(4-fluorobenzyl)oxy]phenyl}-2-methyl-N-(3-thioxo-3H-1,2,4-dithiazol-5-yl)propanamide (Compound 13) (0.081 g, 17%).

$^1$H-NMR(CDCl$_3$) δ 9.06(1H, brs), 7.42(2H, dd), 7.25(2H, d), 7.10(2H, t), 6.99(2H, d), 5.04(2H, s), 1.67(6H, s).

Example 14

2-{4-[(4-Fluorobenzyl)oxy]phenyl}-N-(3-thioxo-3H-1,2,4-dithiazol-5-yl)propanamide (Compound 14)

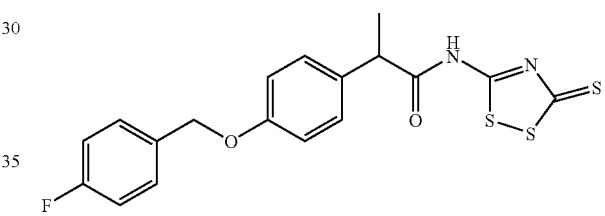

(a) Methyl 2-{4-[(4-fluorobenzyl)oxy]phenyl}propanoate (0.269 mg, 0.932 mmol) obtained in Example 13(b) was dissolved in a mixture of methanol (4 ml) and tetrahydrofuran (4 ml), and 1N potassium hydroxide (2 ml) was added thereto. After being refluxed for 3 hours, the mixture was acidified with 3N hydrochloric acid, and then extracted with ethyl acetate. The organic layer was washed with saturated brine and dried over MgSO$_4$, and then the solvent was evaporated out.

(b) The obtained residue was dissolved in tetrahydrofuran (3.1 ml), and 1,1'-carbonyidiimidazole (0.180 g, 1.11 mmol) was added thereto. The imidazole mixture was stirred for 1 hour at room temperature. Sodium hydride (60% oil suspension 0.044, 1.11 mmol) was suspended in tetrahydrofuran (3.1 ml), and 3-amino-1,2,4-dithiazole-5-thione (0.167 g, 1.11 mmol) was added thereto. After being stirred for 30 minutes at 0° C., the reaction mixture, with the imidazole mixture added thereto, was stirred for 17 hours at room temperature. The reaction mixture, with saturated ammonium chloride water added thereto, was extracted with ethyl acetate. The organic layer was washed with saturated sodium bicarbonate water and saturated brine successively, dried over MgSO$_4$, and then concentrated. The obtained residue was purified by silica gel column chromatography (chloroform:hexane=4:1), to give 2-{4-[(4-fluorobenzyl)oxy]phenyl}-N-(3-thioxo-3H-1,2,4-dithiazol-5-yl)propanamide (Compound 14) (0.275 g, 73%).

$^1$H-NMR(DMSO-d$_6$) δ 7.48(2H, dd), 7.26(2H, d), 7.20 (2H, t), 7.00(2H, d), 5.07(2H, s), 3.99(1H, q), 1.45(3H,d).

Example 15

2-{4-[(4-Fluorobenzyl)oxy]phenyl}-2-[(2-methoxyethoxy)methoxy]-N-(3-thioxo-3H-1,2,4-dithiazol-5-yl)acetoamide (Compound 15)

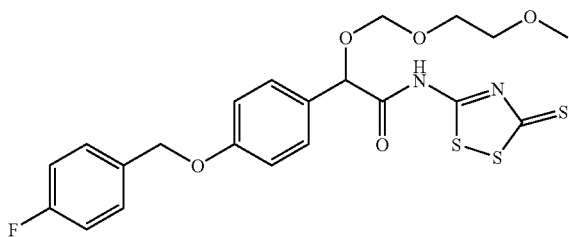

(a) DL-4-hydroxymandelic acid (4.20 g, 24.98 mmol) was dissolved in methanol (50 ml), and sulfuric acid (0.67 ml) was added thereto. The mixture was stirred for 15 hours at room temperature, and then the solvent was evaporated out. The residue was diluted with water, neutralized with sodium hydrogencarbonate, and then extracted with ethyl acetate. The organic layer was washed with saturated brine and dried over $MgSO_4$, and then the solvent was evaporated out.

(b) The obtained residue was dissolved in acetone (44 ml), and potassium carbonate (3.35 g, 24.21 mmol) and 4-fluorobenzyl chloride (2.89 ml, 24.21 mmol) were added thereto. After being refluxed for 26 hours, the mixture, with water added thereto, was extracted with ethyl acetate. The organic layer was washed with saturated brine and dried over $MgSO_4$, and then the solvent was evaporated out. The obtained residue was purified by silica gel column chromatography (20% ethyl acetate/hexane), to give methyl 2-{4-[(4-fluorobenzyl)oxy]phenyl}-2-hydroxyacetate (1.00 g, 14%).

$^1$H-NMR(CDCl$_3$) δ 7.39(2H, dd), 7.33(2H, d), 7.07(2H, t), 6.95(2H, d), 5.12(1H, d), 5.02(2H, s), 3.76(3H, s), 3.36(1H, d).

(c) Methyl 2-{4-[(4-fluorobenzyl)oxy]phenyl}-2-hydroxyacetate (0.507 g, 1.75 mmol) was dissolved in tetrahydrofuran (9 ml), and sodium hydride (0.09 g, 2.27 mmol) was added thereto while being cooled with ice. The mixture was stirred for 30 minutes at room temperature, and 2-methoxyethoxymethylchloride (0.26 ml, 2.27 mmol) was added thereto while being cooled with ice. After being stirred for 62 hours at room temperature, the mixture, with water added thereto, was extracted with ethyl acetate. The organic layer was dried over $MgSO_4$, and then the solvent was evaporated out. The obtained residue was purified by silica gel column chromatography (30% ethyl acetate/hexane), to give methyl 2-{4-[(4-fluorobenzyl)oxy]phenyl}-2-[(2-methoxyethoxy)methoxy]acetate (0.421 g, 64%).

$^1$H-NMR(CDCl$_3$) δ 7.41-7.36(4H, m), 7.07(2H, t), 6.94(2H, d), 5.18(1H, s), 5.01(2H, s), 4.82(1H, d), 4.75(1H, d), 3.74-3.72(2H, m), 3.71(3H, s), 3.58-3.55(2H, m), 3.37(3H, s).

(d) Methyl 2-{4-[(4-fluorobenzyl)oxy]phenyl}-2-[(2-methoxyethoxy)methoxy]acetate (0.421 g, 1.11 mmol) was dissolved in a mixture of methanol (6 ml) and tetrahydrofuran (6 ml), and 1N sodium hydroxide (3 ml) was added thereto. After being stirred for 1 hour at room temperature, the reaction mixture was neutralized and then extracted with ethyl acetate. The organic layer dried over $MgSO_4$, and then the solvent was evaporated out. The obtained residue was purified by silica gel column chromatography (50% ethyl acetate/hexane), to give 2-{4-[(4-fluorobenzyl)oxy]phenyl}-2-[(2-methoxyethoxy)methoxy]acetic acid (0.156 g, 39%).

$^1$H-NMR(CDCl$_3$) δ 7.40-7.35(4H, m), 7.07(2H, t), 6.95(2H, d), 5.20(1H, s), 5.01(2H, s), 4.81(1H, d), 4.73(1H, d), 3.82-3.78(1H, m), 3.73-3.67(1H, m), 3.57-3.51(2H, m), 3.37(3H, s).

(e) 2-{4-[(4-Fluorobenzyl)oxy]phenyl}-2-[(2-methoxyethoxy)methoxy]acetic acid (0.156 g, 0.429 mmol) was dissolved in tetrahydrofuran (1.4 ml), and 1,1'-carbonyidiimidazole (0.083 g, 0.514 mmol) was added thereto. The imidazole mixture was stirred1 hour at room temperature. Sodium hydride (60% oil suspension 0.021 g, 0.514 mmol) was suspended in tetrahydrofuran (1.4 ml), and 3-amino-1,2,4-dithiazole-5-thione (0.077 g, 0.514 mmol) was added thereto. After being stirred for 30 minutes at 0° C., the reaction mixture, with the imidazole mixture added thereto, was stirred for 16 hours at room temperature. The reaction mixture, with saturated ammonium chloride water added thereto, was extracted with ethyl acetate. The organic layer was washed with saturated brine, dried over $MgSO_4$, and then concentrated. The obtained residue was purified by silica gel column chromatography (chloroform), to give 2-{4-[(4-fluorobenzyl)oxy]phenyl}-2-[(2-methoxyethoxy)methoxy]-N-(3-thioxo-3H-1,2,4-dithiazol-5-yl)acetoamide (Compound 15) (0.139 g, 65%).

$^1$H-NMR(CDCl$_3$) δ 7.39(2H, dd), 7.32(2H, d), 7.07(2H, t), 6.99(2H, d), 5.40(1H, s), 5.03(2H, s), 4.80(1H, d), 4.72(1H, d), 3.74-3.70(2H, m), 3.58-3.55(2H, m), 3.40(3H, s).

Example 16

2-{4-[(4-Fluorobenzyl)oxy]phenyl}-2-hydroxy-N-(3-thioxo-3H-1,2,4-dithiazol-5-yl) acetoamide (Compound 16)

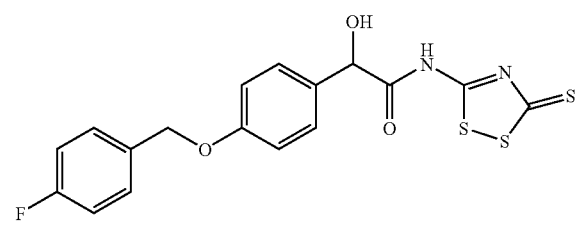

2-{4-[(4-Fluorobenzyl)oxy]phenyl}-2-[(2-methoxyethoxy)methoxy]-N-(3-thioxo-3H-1,2,4-dithiaxol-5-yl)acetoamide (0.073 g, 0.146 mmol) was dissolved in dichloromethane (0.7 ml), and trifluoroacetic acid (0.03 ml, 0.438 mmol) was added thereto. After being stirred for 4 days at room temperature, the reaction mixture, with chloroform added thereto, was washed with saturated sodium bicarbonate water and saturated brine successively. The organic layer was dried over $MgSO_4$ and then concentrated. The obtained residue was purified by silica gel column chromatography (1% methanol/chloroform), to give 2-{4-[(4-fluorobenzyl) oxy]phenyl}-2-hydroxy-N-(3-thioxo-3H-1,2,4-dithiazol-5-yl)acetoamide (Compound 16) (0.015 g, 25%).

$^1$H-NMR(DMSO-d$_6$) δ 12.02(1H, brs), 7.49(2H, dd), 7.32(2H, d), 7.21(2H, t), 7.07(2H, d), 5.96(1H, s), 5.12(2H, s).

Compounding Example 1

Cream

| | |
|---|---|
| (1)Stearic acid | 5.0 weight % |
| (2)Stearyl alcohol | 4.0 |
| (3)Isopropyl myristate | 18.0 |
| (4)Glyceryl monostearate | 3.0 |
| (5)Propylene glycol | 10.0 |
| (6)Compound 1 | 0.001 |
| (7)Vitamin E acetate | 0.05 |
| (8)Potassium hydroxide | 0.2 |
| (9)Sodium hydrogensulfite | 0.01 |
| (10)Phenoxyethanol | 0.02 |
| (11)Perfume | q.s. |
| (12)Ion-exchange water | Balance |

(Preparing Method)

(5) and (8) were added and dissolved into (12), and then heated and maintained at 70° C. (a water phase). On the other hand, (1)-(4), (6), (7) and (9)-(11) were mixed together, melted with heating, and then maintained at 70° C. (a oil phase). The oil phase was added to the water phase slowly, and the mixture was kept at the temperature for a while. Then, the mixture was emulsified by a homomixer to be uniform, and then cooled to 30° C. while being mixed well, to give a cream.

Compounding Example 2

Cream

| | |
|---|---|
| (1)Stearic acid | 2.0 weight % |
| (2)Stearyl alcohol | 7.0 |
| (3)Hydrogenated lanolin | 2.0 |
| (4)Squalane | 5.0 |
| (5)2-Octyldodecyl alcohol | 6.0 |
| (6)POE(25)cetyl ether | 3.0 |
| (7)Glyceryl monostearate | 2.0 |
| (8)Propylene glycol | 5.0 |
| (9)Magnesium ascorbylphosphate | 0.1 |
| (10)Compound 2 | 0.001 |
| (11)Sodium hydrogensulfite | 0.03 |
| (12)Ethylparaben | 0.3 |
| (13)Perfume | q.s. |
| (14)Ion-exchange water | Balance |

(Preparing Method)

(8) and (9) were added to (14), and then heated and maintained at 70° C. (a water phase). On the other hand, (1)-(7) and (10)-(13) were mixed together, melted with heating, and then maintained at 70° C. (a oil phase). The oil phase was added to the water phase, and the mixture was pre-emulsified. Then, the mixture was emulsified by a homomixer to be uniform, and cooled to 30° C. while being mixed well, to give a cream.

Compounding Example 3

Cream

| | |
|---|---|
| (1)Solid paraffin | 5.0 weight % |
| (2)Beeswax | 10.0 |
| (3)Vaseline | 15.0 |
| (4)Liquid paraffin | 41.0 |
| (5)Glyceryl monostearate | 2.0 |
| (6)POE(20)sorbitan monolaurate | 2.0 |
| (7)Soap powder | 0.1 |
| (8)Borax | 0.2 |
| (9)Soybean lysolecithin | 0.1 |
| (10)Compound 3 | 0.01 |
| (11)Sodium hydrogensulfite | 0.03 |
| (12)Ethylparaben | 0.3 |
| (13)Perfume | q.s. |
| (14)Ion-exchange water | Balance |

(Preparing Method)

(7), (8) and (9) were added to (14), and then heated and maintained at 70° C. (a water phase). On the other hand, (1)-(6) and (10)-(13) were mixed together, melted with heating, and then maintained at 70° C. (a oil phase). The oil phase was added to the water phase, and the mixture was pre-emulsified. Then, the mixture was emulsified by a homomixer to be uniform, and cooled to 30° C. while being mixed well, to give a cream.

Compounding Example 4

Milky Lotion

| | |
|---|---|
| (1)Stearic acid | 2.5 weight % |
| (2)Cetyl alcohol | 1.5 |
| (3)Vaseline | 5.0 |
| (4)Liquid paraffin | 10.0 |
| (5)POE(10)monooleate | 2.0 |
| (6)Polyethylene glycol 1500 | 3.0 |
| (7)Triethanolamine | 1.0 |
| (8)Carboxyvinyl polymer (Carbopol 941, B. F. Goodrich 社) | 0.05 |
| (9)Beech but extract | 0.1 |
| (10)Compound 5 | 0.001 |
| (11)Sodium hydrogensulfite | 0.01 |
| (12)Ethylparaben | 0.3 |
| (13)Perfume | q.s. |
| (14)Ion-exchange water | Balance |

(Preparing Method)

(8) was dissolved in a small amount of (14) (Phase A). On the other hand, (6), (7) and (9) were added to the rest of (14), dissolved with heating, and then maintained at 70° C. (a water phase). (1)-(5) and (10)-(13) were mixed together, melted with heating, and then maintained at 70° C. (a oil phase). The oil phase was added to the water phase, and the mixture was pre-emulsified. Then, the mixture, with the Phase A added thereto, was emulsified by a homomixer to be uniform, and cooled to 30° C. while being mixed well, to give a milky lotion.

Compounding Example 5

Milky Lotion

| | | |
|---|---|---|
| (1)Microcrystalline wax | 1.0 weight % | |
| (2)Beeswax | 2.0 | |
| (3)Lanolin | 20.0 | |
| (4)Liquid paraffin | 10.0 | |
| (5)Squalane | 5.0 | |
| (6)Sorbitan sesquioleate | 4.0 | |
| (7)POE(20)sorbitan monooleate | 1.0 | |
| (8)Propylene glycol | 7.0 | |
| (9)Gambir extract | 0.1 | |
| (10)Compound 6 | 2.0 | |
| (11)Sodium hydrogensulfite | 0.01 | |
| (12)Ethylparaben | 0.3 | |
| (13)Perfume | q.s. | |
| (14)Ion-exchange water | Balance | |

(Preparing Method)

(8) and (9) were added to (14), and then heated and maintained at 70° C. (a water phase). On the other hand, (1)-(7) and (10)-(13) were mixed together, melted with heating, and then maintained at 70° C. (a oil phase). The water phase was added to the oil phase slowly while being mixed. The mixture was emulsified by a homomixer to be uniform, and cooled to 30° C. while being mixed well, to give a milky lotion.

Compounding Example 6

Gel

| | | |
|---|---|---|
| (1)95% Ethanol | 10.0 weight % | |
| (2)Dipropylene glycol | 15.0 | |
| (3)POE(50)oleyl ether | 2.0 | |
| (4)Carboxyvinyl polymer (Carbopol 941, B. F. Goodrich 社) | 1.0 | |
| (5)Sodium hydroxide | 0.15 | |
| (6)L-Arginine | 0.1 | |
| (7)Compound 7 | 1.0 | |
| (8)Vitamin E acetate | 0.05 | |
| (9)Sodium 2-hydroxy-4-methoxybenzophenone sulfonate | 0.05 | |
| (10)Trisodium ethylenediamine tetraacetate 2-hydrate | 0.05 | |
| (11)Methylparaben | 0.2 | |
| (12)Perfume | q.s. | |
| (13)Ion-exchange water | Balance | |

(Preparing Method)

(4) was dissolved in (13) uniformly (a water phase). On the other hand, (3), (7) and (8) were dissolved in (1), and the mixture was added to the water phase. Then, (2) and (9)-(12) were added thereto, and the mixture was neutralized with (5) and (6), to give a gel.

Compounding Example 7

Essence

| Phase A: | | |
|---|---|---|
| 95% Ethanol | 10.0 weight % | |
| POE(20)octyldodecanol | 1.0 | |
| Pantothenyl ethyl ether | 0.1 | |
| Compound 8 | 1.0 | |
| Methylparaben | 0.15 | |
| Phase B: | | |
| Potassium hydroxide | 0.1 | |
| Phase C: | | |
| Glycerin | 5.0 | |
| Dipropylene glycol | 10.0 | |
| Sodium hydrogensulfite | 0.03 | |
| Carboxyvinyl polymer (Carbopol 940, B. F. Goodrich 社) | 0.2 | |
| Magnesium ascorbylphosphate | 0.1 | |
| Soybean lysolecithin | 0.1 | |
| Purified water | Balance | |

(Preparing Method)

Phase A and Phase C were each dissolved uniformly. Phase C was added and solubilized into Phase A, and then Phase B added thereto. The mixture was filled up in a container, to give an essence.

Compounding Example 8

Pack

| Phase A: | | |
|---|---|---|
| Dipropylene glycol | 5.0 weight % | |
| POE(60)hardened caster oil | 5.0 | |
| Phase B: | | |
| Compound 1 | 0.01 | |
| Olive oil | 5.0 | |
| Tocopherol acetate | 0.2 | |
| Ethylparaben | 0.2 | |
| Perfume | 0.2 | |
| Phase C: | | |
| Sodium hydrogensulfite | 0.03 | |
| Polyvinyl alcohol (saponification degree 90, polymerization degree 2000) | 13.0 | |
| Ethanol | 7.0 | |
| Soybean lysolecithin | 0.1 | |
| Beech buds extract | 0.1 | |
| Purified water | Balance | |

(Preparing Method)

Phase A, Phase B and Phase C were each dissolved uniformly. Phase A was added and solubilized into Phase B, and then Phase B added thereto. The mixture was filled up in a container, to give a pack.

Compounding Example 9

Solid Foundation

| | | |
|---|---|---|
| (1)Talc | 43.0 weight % | |
| (2)Kaolin | 15.0 | |
| (3)Sericite | 10.0 | |
| (4)Zinc oxide | 7.0 | |
| (5)Titanium dioxide | 3.6 | |
| (6)Yellow iron oxide | 2.9 | |

-continued

| | |
|---|---|
| (7) Black iron oxide | 0.2 |
| (8) Squalane | 8.0 |
| (9) Isostearic acid | 4.0 |
| (10) POE sorbitan monooleate | 3.0 |
| (11) Isocetyl octanoate | 2.0 |
| (12) Vitamin E acetate | 0.05 |
| (13) Compound 2 | 1.0 |
| (14) Beech buds extract | 0.1 |
| (15) Antiseptics | q.s. |
| (16) Perfume | q.s. |

(Preparing Method)

Powder components of (1)-(7) were mixed by a blender thoroughly, and then oil components of (8)-(13) and components of (14)-(16) were added and well-kneaded therein. The mixture was filled up and formed in a container, to give a solid foundation.

Compounding Example 10

Emulsion Type Foundation (Cream Type)

| | |
|---|---|
| Powder part: | |
| Titanium dioxide | 10.3 weight % |
| Sericite | 5.4 |
| Kaolin | 3.0 |
| Yellow iron oxide | 0.8 |
| Red iron oxide | 0.3 |
| Black iron oxide | 0.2 |
| Oil phase: | |
| Decamethylcyclopentasiloxane | 11.0 |
| Liquid paraffin | 4.4 |
| POE dimethylpolysiloxane | 4.0 |
| Compound 3 | 1.0 |
| Octyl methoxycinnamate | 0.5 |
| Vitamin E acetate | 0.05 |
| Water phase: | |
| Purified water | 51.0 |
| 1,3-Butylene glycol | 4.5 |
| Sorbitan sesquioleate | 3.0 |
| Gambir extract | 0.1 |
| Antiseptics | q.s. |
| Perfume | q.s. |

(Preparing Method)

The water phase components except for perfume were stirred together with heating, and the powder, which was mixed and grinded thoroughly, was added thereto. The mixture was treated by a homomixer, and then the oil phase, which was mixed with heating, was added thereto. After being treated by the homomixer, the mixture, with perfume added thereto while being stirred, was cooled to room temperature, to give a emulsion type foundation.

In the following, Examples of dithiazole compounds and manufacturing methods thereof in accordance with the present invention will be shown.

Compound 17

4-Methyl-N-[4-[[[2-oxo-2-[(3-thioxo-3H-1,2,4-dithiazol-5-yl)amino]ethyl]amino]sulfonyl]phenyl]benzamide

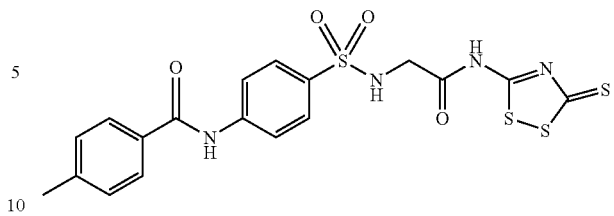

Glycine tert-butyl ester hydrochloride is reacted with 4-nitrobenzenesulfonyl chloride in pyridine, to give tert-butyl 2-{[(4-nitrophenyl)sulfonyl]amino}acetate.

This compound is subjected to a catalytic reduction using Pd—C in ethanol, to give tert-butyl 2-{[(4-aminophenyl)sulfonyl]amino}acetate.

This compound is reacted with p-toluoyl chloride in pyridine, to give tert-butyl 2-[[[4-[(4-methylbenzoyl)amino]phenyl]sulfonyl]amino]acetate.

Water and trifluoroacetic acid are added and reacted to this compound, to give 2-[[[4-[(4-methylbenzoyl)amino]phenyl]sulfonyl]amino]acetic acid.

N-Methylmorpholine, N-hydroxybenzotriazole and 1-ethyl-3-(3'-dimethylamino propyl)carbodiimide hydrochloride are added and reacted to a solution of this compound in N,N-dimethylformamide, to give the captioned compound.

Compound 18

N-[4-[[[1-Benzyl-2-oxo-2-[(3-thioxo-3H-1,2,4-dithiazol-5-yl)amino]ethyl]amino]sulfonyl]phenyl]benzamide

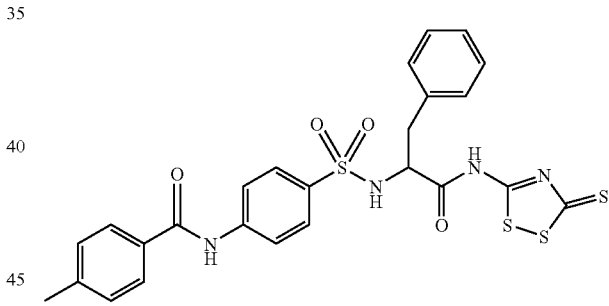

Phenylalanine tert-butyl ester hydrochloride is reacted with 4-nitrobenzenesulfonyl chloride in pyridine, to give tert-butyl 2-{[4-nitrophenyl]sulfonyl}amino}-3-phenylpropanoate.

This compound is subjected to a catalytic reduction using Pd—C in ethanol, to give tert-butyl 2-{[(4-aminophenyl)sulfonyl]amino}-3-phenylpropanoate.

This compound is reacted with p-toluoyl chloride in pyridine, to give tert-butyl 2-[[[4-[(4-methylbenzoyl)amino]phenyl]sulfonyl]amino]-3-phenylpropanoate.

Water and trifluoroacetic acid are added and reacted to this compound, to give 2-[[[4-[(4-methylbenzoyl)amino]phenyl]sulfonyl]amino]-3-phenylpropionic acid.

N-Methylmorpholine, N-hydroxybenzotriazole and 1-ethyl-3-(3'-dimethylamino propyl)carbodiimide hydrochloride are added and reacted to a solution of this compound in N,N-dimethylformamide, and further reacted with 3-amino-1,2,4-dithiazole-5-thione, to give the captioned compound.

Compound 19
2-{[(4-Methoxyphenylsulfonyl](3-pyridinylmethyl)
   amino}-3-methyl-N-(3-thioxo-3H-1,2,4-dithiazol-5-yl)
   butanamide

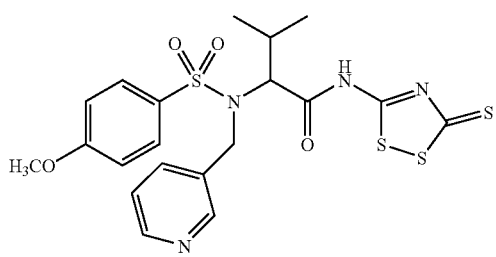

Valine tert-butyl ester hydrochloride is reacted with 4-methoxybenzenesulfonyl chloride in dichloromethane in the presence of triethylamine, to give tert-butyl 2-{[(4-methoxyphenyl)sulfonyl]amino}-3-methylbutanoate.

This compound is reacted with 3-(chloromethyl)pyridine hydrochloride in DMF in the presence of potassium carbonate, to give tert-butyl 2-{[(4-methoxyphenyl)sulfonyl](3-pyridinylmethyl)amino}-3-methylbutanoate.

This compound was subjected to a deprotecting reaction with 4N hydrochloric acid-dioxane added thereto, to give 2-{[(4-methoxyphenyl)sulfonyl](3-pyridinylmethyl)amino}-3-methylbutanoic acid salt.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and then further reacted with 3-amino-1,2,4-dithiazole-5-thione, to give the captioned compound.

Compound 20
1-[(4-Methoxyphenyl)sulfonyl]-N-(3-thioxo-3H-1,2,4-
   dithiazol-5-yl)-2-pyrrolidine carboxamide

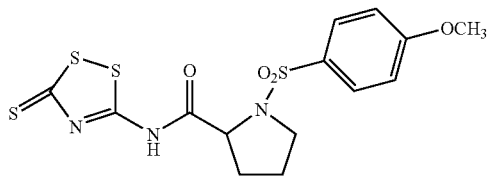

Proline is reacted with 4-methoxybenzenesulfonyl chloride in dichloromethane in the presence of triethylamine, to give 1-[(4-methoxyphenyl)sulfonyl]-2-pyrrolidinecarboxylic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 21
2-[(4-Methoxyphenyl)sulfonyl]-N-(3-thioxo-3H-1,2,4-
   dithiazol-5-yl)-1,2,3,4-tetrahydro-3-isoquinolinecarboxamide

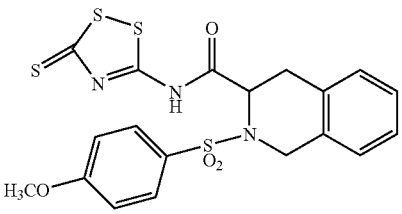

1,2,3,4-Tetrahydro-3-isoquinolinecarboxylic acid hydrochloride is reacted with 4-methoxybenzenesulfonyl chloride in dichloromethane in the presence of triethylamine, to give 2-[(4-methoxyphenyl)sulfonyl]-1,2,3,4-tetrahydro-3-isoquinoline carboxylic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 22
4-[(4-Methoxyphenyl)sulfonyl]-N-(3-thioxo-3H-1,2,4-
   dithiazol-5-yl)-3-morpholine carboxamide

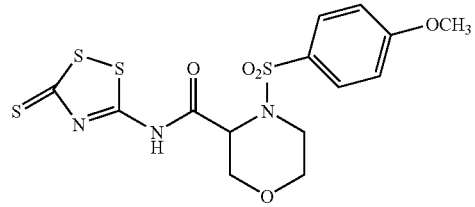

3-Morpholinecarboxylic acid is reacted with 4-methoxybenzenesulfonyl chloride in dichloromethane in the presence of triethylamine, to give 4-[(4-methoxyphenyl) sulfonyl]-3-morpholinecarboxylic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 23
2-[3-[[4-(Benzyloxy)benzyl]oxy]-5-methoxy-2-propylphenyl]-N-(3-thioxo-3H-1,2,4-dithiazol-5-yl)acetoamide

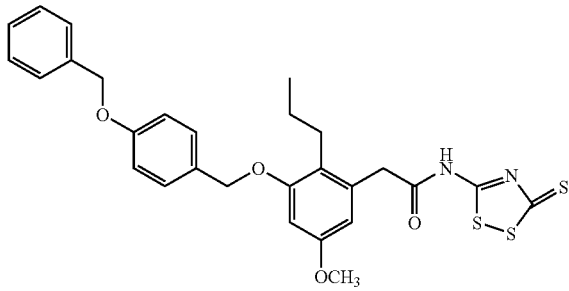

2-(3-Hydroxy-5-methoxy-2-propylphenyl)acetic acid is refluxed in methanol in the presence of sulfuric acid, to give methyl 2-(3-hydroxy-5-methoxy-2-propylphenyl)acetate.

This compound is reacted with 4-benzyloxybenzyl chloride in acetone in the presence of potassium carbonate, to give methyl 2-[3-[[4-(benzyloxy)benzyl]oxy]-5-methoxy-2-propylphenyl]acetate.

This compound is treated with 1N potassium hydroxide in methanol, to give 2-[3-[[4-(benzyloxy)benzyl]oxy]-5-methoxy-2-propylphenyl]acetic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 24

2-{3,4-Bis[(4-methoxybenzyl)oxy]phenyl}-N-(3-thioxo-3H-1,2,4-dithiazol-5-yl) acetoamide

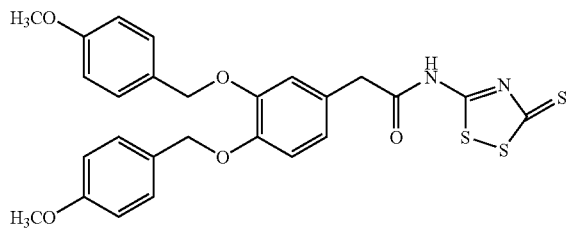

3,4-Dihydroxyphenylacetic acid is refluxed in methanol in the presence of sulfuric acid, to give methyl 2-(3,4-dihydroxyphenyl)acetate.

This compound is reacted with 4-methoxybenzyl chloride in acetone in the presence of potassium carbonate, to give methyl 2-{3,4-bis[(4-methoxybenzyl)oxy]phenyl}acetate.

This compound is treated with 1N potassium hydroxide in methanol, to give 2-{3,4-bis[(4-methoxybenzyl)oxy]phenyl}acetic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 25

2-[4-[2-(2-Methoxyethoxy)ethoxy]-3-[[(4-methoxyphenyl)sulfonyl]amino]phenyl]-N-(3-thioxo-3H-1,2,4-dithiazol-5-yl)acetoamide

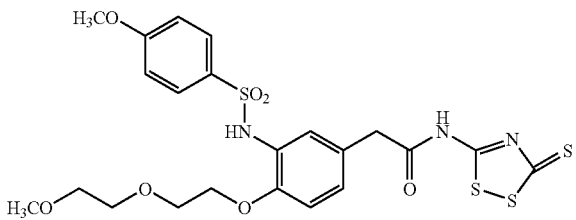

Ethyl(3-amino-4-hydroxyphenyl)acetate is reacted with 4-methoxybenzene sulfonyl chloride in chloroform in the presence of triethylamine, to give ethyl 2-[4-hydroxy-3-[[(4-methoxyphenyl)sulfonyl]amino]phenyl]acetate.

This compound is reacted with 1-bromo2-(2-methoxyethoxy)ethane in acetone in the presence of potassium carbonate, to give ethyl 2-[4-[2-(2-methoxyethoxy)ethoxy]-3-[[(4-methoxyphenyl)sulfonyl]amino]phenyl]acetate.

This compound is treated with 1N potassium hydroxide in methanol, to give 2-[4-[2-(2-methoxyethoxy)ethoxy]-3-[[(4-methoxyphenyl)sulfonyl]amino]phenyl]acetic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 26

2-{3,5-Bis[(4-butoxybenzoyl)amino]-4-[2-(2-methoxyethoxy)ethoxy]phenyl}-N-(3-thioxo-3H-1,2,4-dithiazol-5-yl)acetoamide

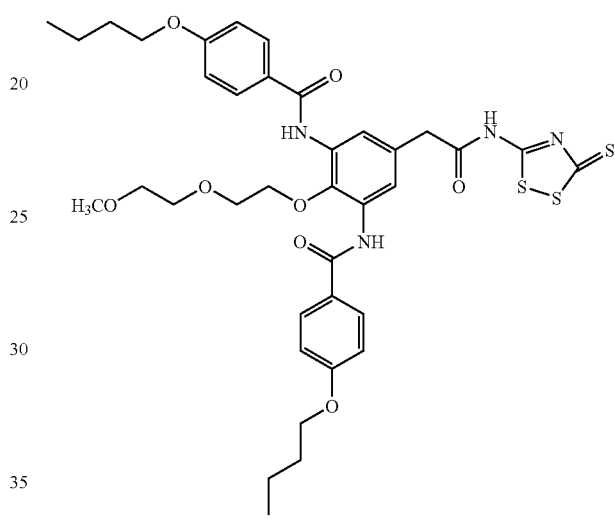

3,5-Dinitro-4-hydroxyphenylacetic acid is refluxed in methanol in the presence of sulfuric acid, to give methyl 2-(3,5-dinitro-4-hydroxyphenyl)acetate.

This compound is reacted in ethanol in the presence of palladium catalyst in hydrogen atmosphere, to give methyl 2-(3,5-diamino-4-hydroxyphenyl)acetate.

This compound is reacted with 4-n-butoxybenzoylchloride in chloroform in the presence of triethylamine, to give methyl 2-{3,5-bis[(4-butoxybenzoyl)amino]-4-hydroxyphenyl}acetate.

This compound is reacted with 1-bromo-2-(2-methoxyethoxy)ethane in acetone in the presence of potassium carbonate, to give methyl 2-{3,5-bis[(4-butoxybenzoyl)amino]-4-[2-(2-methoxyethoxy)ethoxy]phenyl}acetate.

This compound is treated with 1N potassium hydroxide in methanol, to give 2-{3,5-bis[(4-butoxybenzoyl)amino]-4-[2-(2-methoxyethoxy)ethoxy]phenyl}acetic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 27

2-[2,5-Bis(3-pyridinylmethoxy)phenyl]-N-(3-thioxo-3H-1,2,4-dithiazol-5-yl)acetoamide

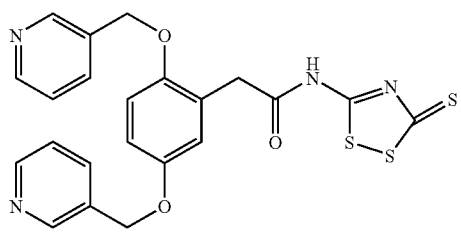

2,5-Dihydroxyphenylacetic acid is refluxed in methanol in the presence of sulfuric acid, to give methyl 2-(2,5-dihydroxyphenyl)acetate.

This compound is reacted with 3-(chloromethyl)pyridine hydrochloride in acetone in the presence of potassium carbonate, to give methyl 2-[2,5-bis(pyridinylmethoxy)phenyl]acetate.

This compound is treated with 1N potassium hydroxide in methanol, to give 2-[2,5-bis(3-pyridinylmethoxy)phenyl]acetic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 28
2-{3,4-Bis[2-(2-methoxyethoxy)ethoxy]phenyl}-2-hydroxy-N-(3-thioxo-3H-1,2,4-dithiazol-5-yl)acetoamide

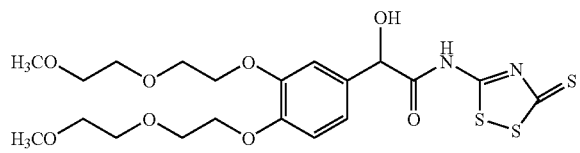

3,4-Dihydroxymandelic acid is refluxed in methanol in the presence of sulfuric acid, to give methyl 2-(3,4-dihydroxyphenyl)-2-hydroxyacetate.

This compound is reacted with 1-bromo-2-(2-methoxyethoxy)ethane in acetone in the presence of potassium carbonate in acetone, to give methyl 2-[3,4-bis[2-(2-methoxyethoxy)ethoxy]phenyl]-2-hydroxyacetate.

This compound is treated with 1N potassium hydroxide in methanol, to give 2-[3,4-bis[2-(2-methoxyethoxy)ethoxy]phenyl]-2-hydroxyacetic acid.

N-Methylmorpholine, N-hydroxybenzotriazole and 1-ethyl-3-(3'-dimethylaminopropyl)carbodiimide hydrochloride are added and reacted to a solution of this compound in N,N-dimethylformamide, and further reacted with 3-amino-1,2,4-dithiazole-5-thione, to give the captioned compound.

Compound 29
2-[4-[[(Methoxyphenyl)sulfonyl]amino]phenyl]-N-(3-thioxo-3H-1,2,4-dithiazol-5-yl) propanamide

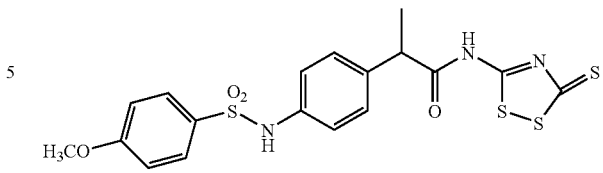

2-(4-Nitrophenyl)propionic acid is refluxed in methanol in the presence of sulfuric acid, to give methyl 2-(4-nitrophenyl)propanoate.

This compound is reacted in the presence of palladium catalyst in ethanol in hydrogen atmosphere, to give methyl 2-(4-aminophenyl)propanoate.

This compound is reacted with 4-methoxybenzenesulfonyl chloride in chloroform in the presence of triethylamine, to give methyl 2-[4-[[(4-methoxyphenyl)sulfonyl]amino]phenyl]propanoate.

This compound is treated with 1N potassium hydroxide in methanol, to give 2-[4-[[(4-methoxyphenyl)sulfonyl]amino]phenyl]propionic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 30
2-[2-(Isobutylamino)-5-methoxy-4-(4-pyridinylmethoxy)phenyl]-N-(3-thioxo-3H-1,2,4-dithiazol-5-yl)acetoamide

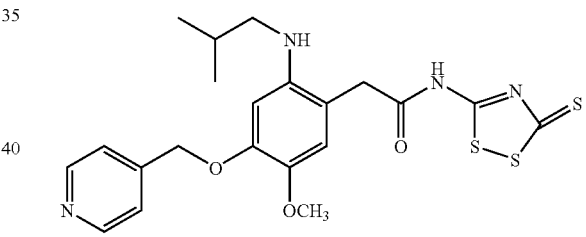

2-Bromo-4-hydroxy-5-methoxyphenylacetic acid is refluxed in methanol in the presence of sulfuric acid, to give methyl 2-(2-bromo-4-hydroxy-5-methoxyphenyl)acetate.

This compound is reacted with 4-chloromethylpyridine hydrochloride in acetone in the presence of potassium carbonate, to give methyl 2-[2-bromo-5-methoxy-4-(4-pyridinylmethoxy)phenyl]acetate.

This compound is reacted with isobutylamine in the presence of sodium amide, to give methyl 2-[2-(isobutylamino)-5-methoxy-4-(4-pyridinylmethoxy)phenyl]acetate.

This compound is treated with 1N potassium hydroxide in methanol, to give 2-[2-(isobutylamino)-5-methoxy-4-(4-pyridinylmethoxy)phenyl]acetic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 31
$N^1$-{2,2-Dimethyl-1-[(methylamino)carbonyl]propyl}-2-isobutyl-$N^4$-(3-thioxo-3H-1,2,4-dithiazol-5-yl)succinamide

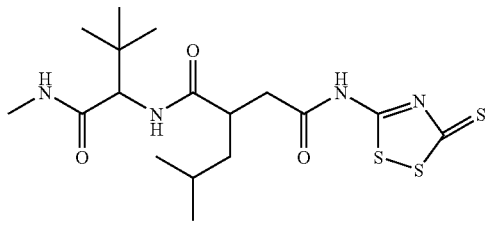

2-Hydroxy-4-methylpentanoic acid is reacted with benzyl bromide in ethyl acetate in the presence of triethylamine, to give benzyl 2-hydroxy-4-methylpentanoate.

This compound is reacted with trifluoromethanesulfonic acid anhydride in pyridine, and further reacted with 1-benzyl 3-(tert-butyl)malonate, to give 1,2-dibenzyl 1-(tert-butyl)4-methyl-1,1,2-pentatricarboxylate.

This compound is subjected to a catalytic reduction in the presence of palladium catalyst in ethanol, to give 2-(tert-butoxycarbonyl)-3-isobutylsuccinic acid.

This compound is refluxed in toluene in the presence of N-methylmorpholine, to give 2-[2-(tert-butoxy)-2-oxoethyl]-4-methylpentanoic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 2-amino-N,3,3-trimethylbutanamide, to give tert-butyl 3-[[[2,2-dimethyl-1-[(methylamino)carbonyl]propyl] amino]carbonyl]-5-methylhexanoate.

This compound is refluxed with trimethylsilyl trifluoromethanesulfonate in dioxane in the presence of triethylamine, to give 3-[[[2,2-dimethyl-1-[(methylamino)carbonyl]propyl]amino]carbonyl]-5-methylhexanoic acid.

N-Methylmorpholine, N-hydroxybenzotriazole and 1-ethyl-3-(3'-dimethylaminopropyl) carbodiimide hydrochloride are added and reacted to this compound in N,N-dimethylformamide, and further reacted with 3-amino-1,2,4-dithiazole-5-thione, to give the captioned compound.

Compound 32
N⁴-{(2,2-Dimethyl-1-[(methylamino)carbonyl]propyl}-2-[(1,3-dioxo-1,3-dihydro-2H-isoindole-2-yl)methyl]-3-isobutyl-N¹-(3-thioxo-3H-1,2,4-dithiazol-5-yl)succinamide

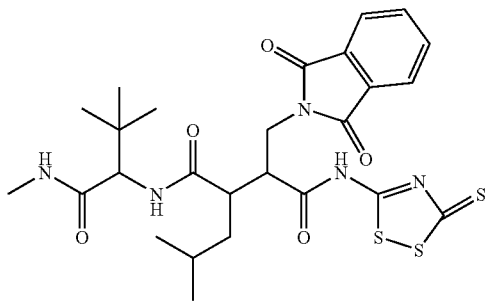

2-Hydroxy-4-methylpentanoic acid is reacted with benzyl bromide in ethyl acetate in the presence of triethylamine, to give benzyl 2-hydroxy-4-methylpentanoate.

This compound is reacted with trifluoromethanesulfonic acid anhydride in pyridine, and further reacted with 1-benzyl 3-(tert-butyl)malonate, to give 1,2-dibenzyl 1-(tert-butyl)4-methyl-1,1,2-pentatricarboxylate.

This compound is reacted with sodium hydride in tetrahydrofuran, and further reacted with N-(bromomethyl)phthalimide, to give 2,3-dibenzyl 2-(tert-butyl) 1-(1,3-dioxo-1,3dihydro-2H-isoindole-2-yl)-5-methyl-2,2,3-hexanetricarboxylate.

This compound is subjected to a catalytic reduction in the presence of palladium catalyst in ethanol, to give 2-(tert-butoxycarbonyl)-2-[(1,3-dioxo-1,3-dihydro-2H -isoindole-2-yl)methyl]-3-isobutylsuccinic acid.

This compound is refluxed in toluene in the presence of N-methylmorpholine, to give 2-{2-(tert-butoxy)-1-[(1,3-dioxo-1,3-dihydro-2H-isoindole-2-yl)methyl]-2-oxoethyl}-4-methylpentanoic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 2-amino-N,3,3-trimethylbutanamide, to give tert-butyl 3-[[[2,2-dimethyl-1-[(methylamino)carbonyl]propyl] amino]carbonyl]-2-[(1,3-dioxo-1,3-dihydro-2H-isoindole-2-yl)methyl]-5-methylhexanoate.

This compound, with trimethylsilyl trifluoromethanesulfonate added thereto, is refluxed in dioxane in the presence of triethylamine, to give 3-[[[2,2-dimethyl-1-[(methylamino)carbonyl]propyl]amino]carbonyl]-2-[(1,3-dioxo-1,3-dihydro-2H-isoindole-2-yl)methyl]-5-methylhexanoic acid.

N-Methylmorpholine, N-hydroxybenzotriazole and 1-ethyl-3-(3'-dimethylaminopropyl) carbodiimide hydrochloride are added and reacted to this compound in N,N-dimethylformamide, and further reacted with 3-amino-1,2,4-dithiazole-5-thione, to give the captioned compound.

Compound 33
N¹-[1-Benzyl-2-(methylamino)-2-oxoethyl]-2-isobutyl-N⁴-(3-thioxo-3H-1,2,4-dithiazol-5-yl)succinamide

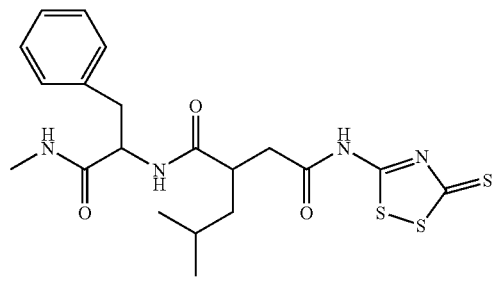

2-Hydroxy-4-methylpentanoic acid is reacted with benzyl bromide in ethyl acetate in the presence of triethylamine, to give benzyl 2-hydroxy-4-methylpentanoate.

This compound is reacted with trifluoromethanesulfonic acid anhydride in pyridine, and further reacted with 1-benzyl 3-(tert-butyl)malonate, to give 1,2-dibenzyl1-(tert-butyl)4-methyl-1,1,2-pentatricarboxylate.

This compound is subjected to a catalytic reduction in the presence of palladium catalyst in ethanol, to give 2-(tert-butoxycarbonyl)-3-isobutylsuccinic acid.

This compound is refluxed in toluene in the presence of N-methylmorpholine, to give 2-[2-(tert-butoxy)-2-oxoethyl]-4-methylpentanoic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 2-amino-N-methyl-3-phenylpropanamide, to give tert-butyl 3-[[[1-benzyl2-(methylamino)-2-oxoethyl]amino]carbonyl]-5-methylhexanoate.

This compound, with trimethylsilyl trifluoromethanesulfonate added thereto, is refluxed in dioxane in the presence of triethylamine, to give 3-[[[1-benzyl-2-(methylamino)-2-oxoethyl]amino]carbonyl]-5-methylhexanoic acid.

N-Methylmorpholine, N-hydroxybenzotriazole and 1-ethyl-3-(3'-dimethylaminopropyl) carbodiimide hydrochloride are added and reacted to this compound in N,N-dimethylformamide, and further reacted with 3-amino-1,2,4-dithiazole-5-thione, to give the captioned compound.

Compound 34

4-Butyl-N-[4-[[[1-(1H-indolyl-3-ylmethyl)-2-oxo-2-[(3-thioxo-3H-1,2,4-dithiaxol-5-yl) amino]ethyl]amino]sulfonyl]phenyl]benzamide

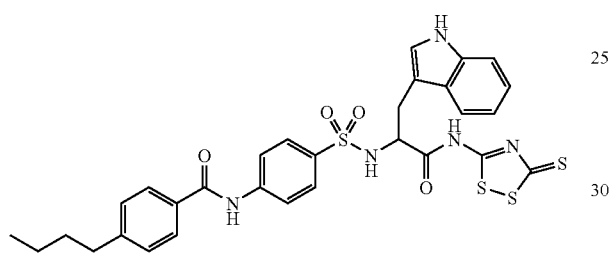

DL-tryptophan methyl ester hydrochloride is reacted with 4-nitrobenzenesulfonyl chloride in pyridine, to give methyl 2-{[(4-nitrophenyl)sulfonyl]amino}-3-(1H-indole-3-yl) propanate.

This compound is subjected to a catalytic reduction using Pd—C in ethanol, to give methyl 2-{[(4-am inophenyl) sulfonyl]amino}-3-(1H-indole-3-yl)propanate.

This compound is reacted with 4-n-butylbenzoylchloride in pyridine, to give methyl 2-[[[4-[(4-butylbenzoyl)amino] phenyl]sulfonyl]amino]-3-(1H-indole-3-yl)propanate.

This compound is reacted with potassium hydroxide in tetrahydrofuran, to give 2-[[[4-[(4-butylbenzoyl)amino]phenyl]sulfonyl]amino]-3-(1H-indole-3-yl)propionic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 35

2-(4-Anilinophenyl)-2-[(2-methoxyethoxy)methoxy]-N-(3-thioxo-3H-1,2,4-dithiazol-5-yl) acetoamide

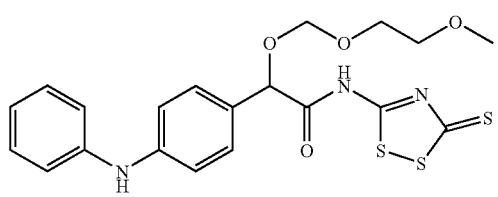

4-Bromomandelic acid, with sulfuric acid added thereto, is reacted in methanol, to give methyl 2-(4-bromophenyl)-2-hydroxyacetate.

This compound is reacted with 2-methoxyethoxymethylchloride in chloroform in the presence of N,N-diisopropylethylamine, to give methyl 2-(4-bromophenyl)-2-[(2-methoxyethoxy)methoxy]acetate.

This compound is reacted with aniline in the presence of copper, potassium iodide and potassium carbonate, to give methyl 2-(4-anilinophenyl)-2-[(2-methoxyethoxy)methoxy] acetate.

This compound is reacted with potassium hydroxide in tetrahydrofuran, to give 2-(4-anilinophenyl)-2-[(2-methoxyethoxy)methoxy]acetic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 36

2-Benzyloxy-2-[4-(4-pyridinylamino)phenyl]-N-(3-thioxo-3H-1,2,4-dithiazol-5-yl) acetoamide

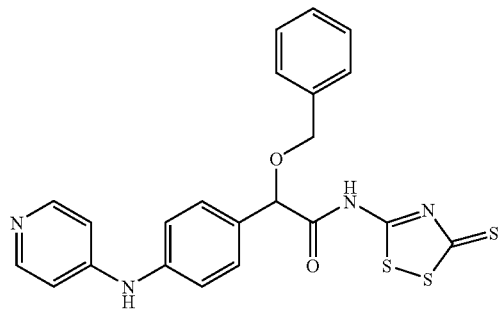

Methyl 2-(4-bromophenyl)-2-hydroxyacetate obtained in said Compound 35 is reacted with benzyl bromide in N,N-dimethylformamide in the presence of sodium hydride, to give methyl 2-benzyloxy-2-(4-bromophenyl)acetoamide.

This compound is reacted with 4-aminopyridine in the presence of copper, potassium iodide and potassium carbonate, to give methyl 2-benzyloxy-2-[4-(4-pyridinylaminophenyl)]acetoamide.

This compound is reacted with potassium hydroxide in tetrahydrofuran, to give 2-benzyloxy-2-[4-(4-pyridinylaminophenyl)]acetic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

Compound 37

2-(Dimethylamino)-2-{4-[(4-methoxybenzyl)oxy]phenyl}-N-(3-thioxo-3H-1,2,4-dithiazol-5-yl)acetoamide

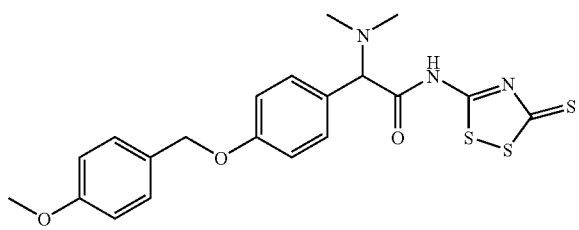

Hydroxyphenylglycine is refluxed in methanol in the presence of sulfuric acid, to give methyl 2-amino2-(4-hydroxyphenyl)acetate.

This compound is reacted with methyl iodide in tetrahydrofuran in the presence of trimethylamine, to give methyl 2-(dimethylamino)-2-(4-hydroxyphenyl)acetate.

This compound is reacted with 4-methoxybenzyl chloride in acetone in the presence of potassium carbonate, to give methyl 2-(dimethylamino)-2-{4-[(4-methoxybenzyl)oxy]phenyl}acetate.

This compound is treated with 1N potassium hydroxide, to give 2-(dimethylamino)-2-{4-[(4-methoxybenzyl)oxy]phenyl}acetic acid.

N-Methylmorpholine, N-hydroxybenzotriazole and 1-ethyl-3-(3'-dimethylaminopropyl) carbodiimide hydrochloride are added and reacted to a solution of this compound in N,N-dimethylformamide, and further reacted with 3-amino-1,2,4-dithiazole-5-thione, to give the captioned compound.

As explained foregoing, since the dithiazole compound (I) of the present invention is effective as a matrix metalloprotease (MMPs) inhibitor, it can be incorporated into various pharmaceutical and cosmetic products. In particular, it can be applied to a skin external composition for the purpose of improving or preventing skin-aging, or to agent for treating or preventing various diseases due to abnormal metabolism of tissue matrix such as arthritis, tissue ulcer formation, metastasis or infiltration of tumor and the like.

What is claimed is:

1. A dithiazole compound or a salt thereof expressed by the following formula (I):

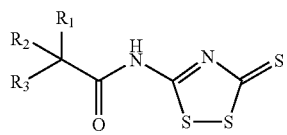

(I)

wherein $R_1$ is hydrogen atom, alkyl, alkenyl, aryl, arylalkyl, heteroarylalkyl, heteroarylthioalkyl, hydroxy, alkoxyalkyl or Het-alkyl (wherein Het is 5-or 6-membered heterocyclic group containing at least one nitrogen atom, and said nitrogen atom is bonded to the alkyl group);

$R_2$ is hydrogen atom, alkyl, aryl, arylalkyl, heteroaryl, heteroarylalkyl, hydroxy, alkoxy, $H(C_xH_{2x}O)_m$— (wherein x is an integer of 1 to 3, and m is an integer of 2 to 5), arylalkoxy, hydroxyalkyl, acyloxyalkyl, alkoxyalkyl, (aryl or heteroaryl)-alkoxyalkyl, alkyl-(thio, sulfinyl or sulfonyl)-alkyl, (amino or alkylamino)-alkyl, acylaminoalkyl, amino, alkylamino, acylamino or Het-alkyl; and $R_3$ is a group expressed by the following formula:

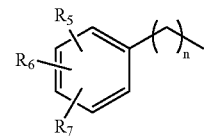

wherein n is 0, $R_5$ and $R_6$ are hydrogen, and $R_7$ is an arylalkoxy.

2. A dithiazole compound or a salt thereof according to claim 1, wherein $R_1$ is hydrogen atom or alkyl; $R_2$ is hydrogen atom, hydroxy, alkyl, alkoxy, $H(C_xH_{2x}O)m$, aryl, arylalkoxy, arylalkyl, heteroarylalkyl, Het-alkyl or alkylamino.

3. A dithiazole compound or a salt thereof according to claim 1, wherein $R_1$ is hydrogen atom or alkyl.

4. A dithiazole compound or a salt thereof according to claim 1, wherein $R_2$ is hydrogen atom, hydroxy, alkyl, $H(C_xH_{2x}O)_m$, aryl, arylalkoxy or alkylamino.

5. A matrix metalloprotease inhibitor comprising, as an active ingredient, a dithiazole compound or a pharmacologically acceptable salt thereof according to claim 1.

6. A cosmetic composition comprising, as an active ingredient, a dithiazole compound or a pharmacologically acceptable salt thereof according to claim 1.

7. A pharmaceutical composition-comprising, as an active ingredient, a dithiazole compound or a pharmacologically acceptable salt thereof according to claim 1.

8. A skin external composition comprising, as an active ingredient, a dithiazole compound or a pharmacologically acceptable salt thereof according to claim 1.

* * * * *